(12) United States Patent
Mao et al.

(10) Patent No.: US 9,597,359 B2
(45) Date of Patent: Mar. 21, 2017

(54) PRODUCTION OF DENTIN, CEMENTUM AND ENAMEL BY CELLS

(75) Inventors: Jeremy J. Mao, Closter, NJ (US); Mo Chen, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 13/877,262

(22) PCT Filed: Oct. 3, 2011

(86) PCT No.: PCT/US2011/054663
§ 371 (c)(1),
(2), (4) Date: Aug. 13, 2013

(87) PCT Pub. No.: WO2012/045097
PCT Pub. Date: Apr. 5, 2012

(65) Prior Publication Data
US 2014/0093481 A1    Apr. 3, 2014

Related U.S. Application Data

(60) Provisional application No. 61/388,820, filed on Oct. 1, 2010, provisional application No. 61/388,894, filed on Oct. 1, 2010.

(51) Int. Cl.
| *A61K 35/32* | (2015.01) |
| *C12N 5/077* | (2010.01) |
| *C12N 5/0775* | (2010.01) |
| *C12N 5/071* | (2010.01) |
| *A61K 35/28* | (2015.01) |
| *A61K 35/36* | (2015.01) |
| *A61K 35/51* | (2015.01) |
| *A61K 35/545* | (2015.01) |
| *A23L 33/10* | (2016.01) |

(52) U.S. Cl.
CPC .............. *A61K 35/32* (2013.01); *A23L 33/10* (2016.08); *A61K 35/28* (2013.01); *A61K 35/36* (2013.01); *A61K 35/51* (2013.01); *A61K 35/545* (2013.01); *C12N 5/0654* (2013.01); *C12N 5/0664* (2013.01); *C12N 5/0697* (2013.01); *A23V 2002/00* (2013.01); *C12N 2500/38* (2013.01); *C12N 2501/39* (2013.01); *C12N 2501/415* (2013.01); *C12N 2501/998* (2013.01); *C12N 2502/13* (2013.01); *C12N 2502/1311* (2013.01); *C12N 2502/1364* (2013.01); *C12N 2533/18* (2013.01)

(58) Field of Classification Search
CPC .............. A23V 2200/312; A61K 31/74; A61K 47/48046; A61K 47/48176; A61K 35/28; A61K 35/32; A61K 35/51; A61K 35/545; C12N 11/08; C12N 9/96; C12N 2501/39; C12N 2502/1311; C12N 2502/1364; C12N 2533/18; C12N 5/0654; C12N 5/0664; C12N 5/0697; C12N 5/077; C12Y 101/03004; C12Y 301/08001
USPC .................. 435/1.1, 373; 525/54.1; 424/93.7
IPC ........... A61K 35/12,35/32, 38/18; C12N 5/077
See application file for complete search history.

(56) References Cited

U.S. PATENT DOCUMENTS

| 5,071,958 | A | 12/1991 | Hammarström et al. |
| 5,098,891 | A | 3/1992 | Hammarström et al. |
| 5,876,454 | A | 3/1999 | Nanci et al. |
| 6,677,306 | B1 | 1/2004 | Veis et al. |
| 6,899,915 | B2 | 5/2005 | Yelick et al. |
| 7,132,015 | B2 | 11/2006 | Wen et al. |
| 7,309,232 | B2 | 12/2007 | Rutherford et al. |
| 2006/0177386 | A1 | 8/2006 | Ueda et al. |
| 2007/0160584 | A1 | 7/2007 | Ueda et al. |
| 2009/0233354 | A1 | 9/2009 | Furcht et al. |
| 2010/0021866 | A1* | 1/2010 | Tsuji et al. ............. 433/215 |
| 2010/0080836 | A1 | 4/2010 | Busch |
| 2010/0093080 | A1 | 4/2010 | Yamaki et al. |
| 2010/0285582 | A1* | 11/2010 | Choung ........... C12N 5/0664 435/375 |

FOREIGN PATENT DOCUMENTS

| EP | 1905459 | 4/2008 |
| EP | 1914300 | 8/2013 |
| WO | WO 2007/013430 | 2/2007 |

OTHER PUBLICATIONS

Kleinman et al. 2005. Matrigel: Basement membrane matrix with biological activity. Seminars in Cancer Biology, vol. 15, pp. 378-386.*
Huang et al. 2003. Mesenchymal Stem Cells Derived from Dental Tissues vs. Those from Other Sources: Their Biology and Role in Regenerative Medicine. Journal of Dental Research 88(9):792-806, 2009, vol. 88, No. 9, pp. 792-806.*
Bakunts et al. 2008. Formation of cardiac fibers in Matrigel matrix. BioTechniques vol. 44:341-348.*
Abe et al., Establishment and Characterization of Rat Dental Epithelial Derived Ameloblast-Lineage Clones, J Biosci Bioeng, 2007, pp. 479-485, vol. 103, No. 5.
(Continued)

*Primary Examiner* — Debbie K Ware
*Assistant Examiner* — Kailash C Srivastava
(74) *Attorney, Agent, or Firm* — Dentons US LLP

(57) ABSTRACT

Described is a method of forming a mineralized material by co-culturing epithelial cell, such as ameloblast, and mesenchymal cell, such as osteoblast or odontoblast, in a mineral-stimulating medium. Also described is a matrix seeded with epithelial cells and mesenchymal cells and infused with a mineral-stimulating medium capable of forming a mineralized material in the matrix. Methods of manufacturing such compositions and methods of treating mineralization-related conditions are also described.

24 Claims, 34 Drawing Sheets

(56) References Cited

OTHER PUBLICATIONS

Chadwick et al., The use of amelogenin protein in the treatment of hard-to-heal wounds, Br. J. of Nursing, 2009, pp. S22-S26, vol. 18, No. 6.

Chen et al., Maintenance of Amelogenin Gene Expression by Transformed Epithelial Cells of Mouse Enamel Organ, Arch Oral Biol., 1992, pp. 771-778, vol. 37, No. 10.

Deutsch et al., High Expression of Human Amelogenin in *E. coli*, Adv Dent Res, 1996, pp. 187-194, vol. 10, No. 2.

Dillon et al., RNAi as an Experimental and Therapeutic Tool to Study and Regulate Physiological and Disease Processes, Annu Rev of Physiol., 2005, pp. 147-173, vol. 67.

Dykxhoorn et al., The Silent Revolution: RNA Interference as Basic Biology, Research Tool, and Therapeutic, Annu Rev of Med., 2005, pp. 401-423, vol. 56.

Elhai et al., Conjugal Transfer of DNA to Cyanobacteria, Methods in Enzymology, 1988, 747-754, vol. 167.

Fan et al., Controlled remineralization of enamel in the prescence of amelogenin and fluride, Biomaterials, 2009, pp. 478-483, vol. 30, No. 4.

Ghadessy et al., Directed evolution of polymerase function by compartmentalized self-replication, Proc Natl Acad Sci., 2001, pp. 4552-4557, vol. 98, No. 8.

Hatakeyama et al., Amelogenin-mediated Regulation of Osteoclastogenesis, and Periodontal Cell Proliferation and Migration, J Dent Res., 2006, pp. 144-149, vol. 85, No. 2.

Helene et al., Control of Gene Expression by Triple Helix-Forming Oligonucleotides, Ann NY Acad Sci., 1992, pp. 27-36, vol. 660.

Huang et al., Bioactive Nanofibers Instruct Cells to Proliferate and Differentiate During Enamel Regeneration, J Bone Miner Res., 2008, pp. 1995-2006, vol. 23, No. 12.

Ikeda et al., Fully functional bioengineered tooth replacement as an organ replacement therapy, PNAS, 2009, pp. 13475-13480, vol. 106, No. 32.

International Search Report and Written Opinion in corresponding International Application No. PCT/US11/54663 dated Feb. 13, 2012, 8 pages.

Kim et al., Regeneration of Dental-Pulp-Like Tissue by Chemotaxis-Induced Cell Horning, Tissue Engineering: Part A, 2010, pp. 3023-3032, vol. 16, No. 10.

Lee et al., Aptamer therapeutics advance, Curr Opin Chem Biol., 2006, pp. 282-289, vol. 10.

Lee et al., CTGF directs fibroblast differentiation from human mesenchymal stem/stromal cells and defines connective tissue healing in a rodent injury model, J Clin Invest., 2010, pp. 3340-3349, vol. 120, No. 9.

Link et al., Beyond toothpicks: new methods for isolating mutant bacteria, Nature Reviews, 2007, pp. 680-688, vol. 5, No. 9.

Maher, DNA Triple-Helix Formation: An Approach to Artificial Gene Repressors?, BioEssays, 1992, pp. 807-815, vol. 14, No. 12.

Mao, Stem Cells and the Future of Dental Care, NY State Dent J., 2008, pp. 20-24, vol. 74, No. 2.

Matsuzawa et al., Putative signaling action of amelogenin utilizes the Wnt/beta-catenin pathway, J Periodontal Res., 2009, pp. 289-296, vol. 44.

Pushparaj et al., Short Interfering RNA (siRNA) as a Novel Therapeutic, Clinical and Experimental Pharmacology and Phys., 2006, pp. 504-510, vol. 33.

Reynolds et al., Rational siRNA design for RNA interference, Nature Biotechnology 2004, pp. 326-330, vol. 22, No. 3.

Romanelli et al., Amelogenin, and extracellular matrix protein, in the treatment of venous leg ulcers and other hard-to-heal wounds: experimental and clinical evidence, Clin Inter. Aging, 2008, pp. 263-272, vol. 3, No. 2.

Sagner et al., Rapid filter assay for the detection of DNA polymerase activity: direct identification of the gene for the DNA polymerase from Thermus aquaticus, Gene, 1991, pp. 119-123, vol. 97.

Sharpe et al., Test-Tube Teeth, Scientific American, 2005, pp. 34-41, vol. 293, No. 2.

Simmer et al., Isolation and Characterization of a Mouse Amelogenin Expressed in *Escherichia coli*, Calcif Tissue Int., 1994, pp. 312-319, vol. 54, No. 4.

Stanford et al., Rapidly Forming Apatitic Mineral in an Osteoblastic Cell Line (UMR 106-01 BSP), J Biol Chem, 1995, pp. 9420-9428, vol. 270, No. 16.

Studier, Protein production by auto-induction in high-density shaking cultures, Protein Expression and Purification, 2005, pp. 207-234, vol. 41, No. 1.

Supplementary European Search Report in corresponding European Application No. EP11830079 dated Feb. 17, 2014, 7 pages.

Takahashi et al., Newly established cell lines from mouse oral epithelium regenerate teeth when combined with dental mesenchyme, In Vitro Cell Dev Biol., 2010, pp. 457-468, vol. 46, No. 5.

Veis et al., Specific Amelogenin Gene Splice Products Have Signaling Effects on Cells in Culture and in Implants in Vivo, J Biol Chem., 2000, pp. 41263-41272, vol. 275, No. 52.

Yagi et al., In Vivo Application of Amelogenin Suppresses Root Resorption, J. Dent. Res., 2009, pp. 176-181, vol. 88, No. 2 and Supplemental data, pp. 1-3.

Yang et al., Clones of Ectopic Stem Cells in the Regeneration of Muscle Defects In Vivo, PloS One, 2010, pp. 1-8, vol. 5, No. 10.

Yildirim et al., Tooth regeneration: a revolution in stomatology and evolution in regenerative medicine, Int J Oral Sci., 2011, pp. 107-116, vol. 3.

Ikeda et al., Growing bioengineered teeth from single cells: potential for dental regenerative medicine, Expert Opin Biol Ther. Jun. 2008; 8(6):735-44.

\* cited by examiner

BF

Fluorescence

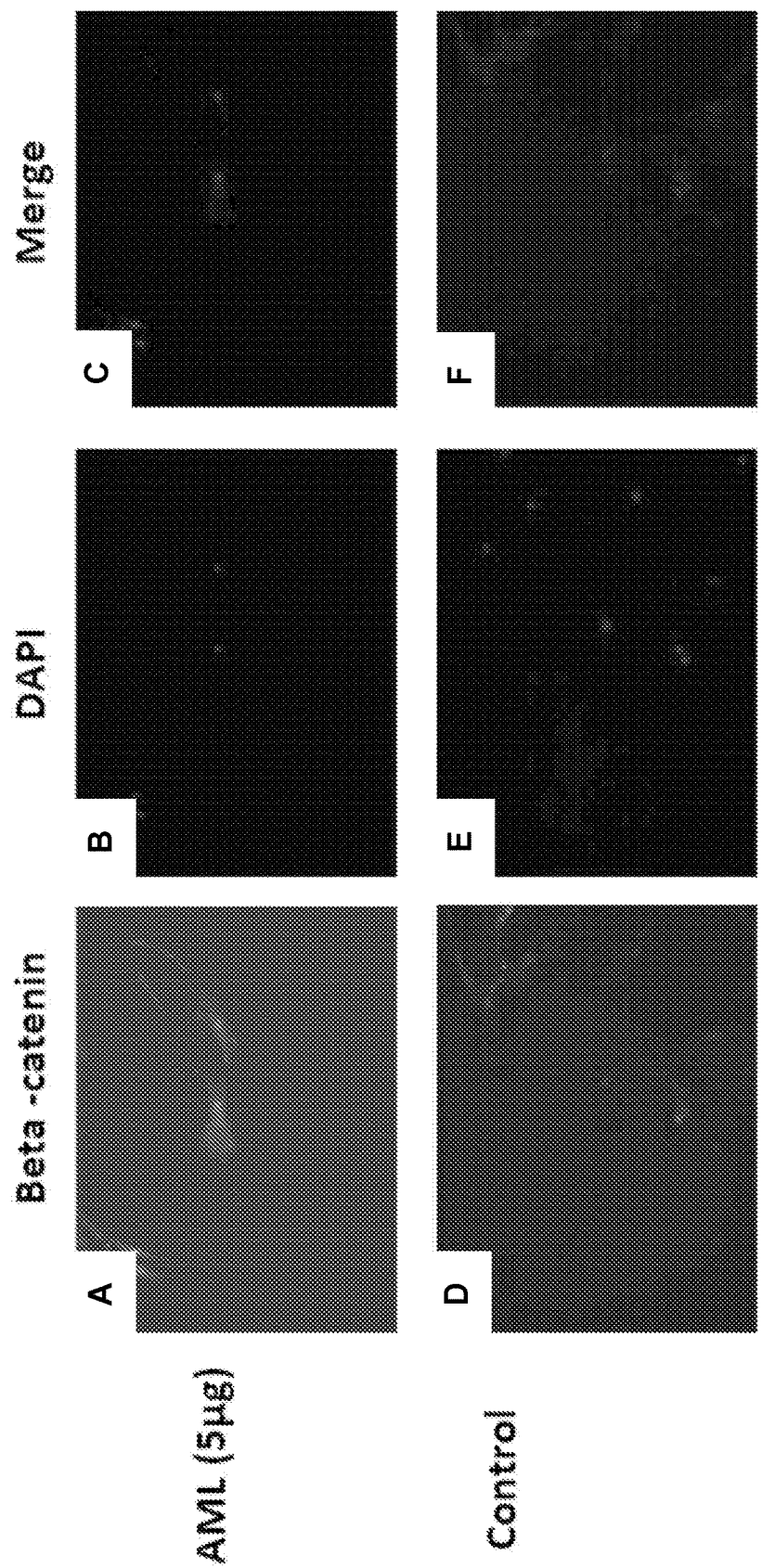

AML treated DSCs

AML stable DSCs

PRODUCTION OF DENTIN, CEMENTUM AND ENAMEL BY CELLS

CROSS-REFERENCE TO RELATED APPLICATIONS

The present application claims the benefit of priority to PCT International Application No. PCT/US11/54663 filed Oct. 3, 2011, which claims the benefit U.S. Provisional Application Ser. No. 61/388,820 filed Oct. 1, 2010, and U.S. Provisional Application Ser. No. 61/388,894 filed Oct. 1, 2010; each of which are incorporated herein by reference in their entireties.

STATEMENT REGARDING FEDERALLY SPONSORED RESEARCH OR DEVELOPMENT

This invention was made with government support under RC2DE020767 awarded by the National Institutes of Health. The government has certain rights in the invention.

MATERIAL INCORPORATED-BY-REFERENCE

Not Applicable.

FIELD OF THE INVENTION

The present invention generally relates to production of dental materials.

BACKGROUND OF THE INVENTION

Epithelial-mesenchymal interaction (EMI) is involved in the development of dental tissues. Odontogenesis or dentin formation is only initiated after ameloblasts provide signaling cues for odontoblasts, and vice versa. But EMI is rarely considered in the regeneration of dental tissues, especially in an approach that can be readily translated into ultimate clinical applications.

Dental restoration uses various synthetic compounds to replace all or parts of teeth (e.g. tooth fillings). Commonly used dental restoration materials, such as mercury amalgam and composite resins, are not always compatible with the human immune system and can be toxic. Substances that naturally occur during tooth formation, such as enamel, dentin, and cementum, are more immunologically compatible, but mass production is not currently feasible due to the small amounts of these substances generated in current systems.

SUMMARY OF THE INVENTION

Provided herein is a novel approach for mass production of dental material, such as dentin and enamel, from progenitor cells. Such approach can yield more robust mineralization as compared to conventional culturing protocols and safer, more immunologically-compatible materials as compared to dental restoration materials.

One aspect provides a method of forming a mineralized material. In some embodiments, the method includes co-culturing epithelial cells and mesenchymal cells in a mineral-stimulating media under conditions suitable to induce production of a mineralized material. In some embodiments, the method includes differentiating progenitor cells to form epithelial cells. In some embodiments, the method includes differentiating progenitor cells to form mesenchymal cells. In some embodiments, the method includes differentiating progenitor cells to form epithelial cells and mesenchymal cells.

Another aspect provides an engineered tissue composition. In some embodiments, the composition includes epithelial cells, mesenchymal cells, a biocompatible matrix, and a mineral-stimulating media. In some embodiments of the composition, the epithelial cells and the mesenchymal cells are seeded in the biocompatible matrix. In some embodiments, the mineral-stimulating media is infused in the biocompatible matrix. In some embodiments, the epithelial cells and the mesenchymal cells are fluidly connected through mineral-stimulating media. In some embodiments of the composition, the epithelial cells and the mesenchymal cells are seeded in the biocompatible matrix, the mineral-stimulating media is infused in the biocompatible matrix, and the epithelial cells and the mesenchymal cells are fluidly connected through mineral-stimulating media.

Another aspect is a method of forming a mineralized composition. In some embodiments, the method includes introducing progenitor cells into a matrix material. In some embodiments, the method includes differentiating a first portion of the progenitor cells to form epithelial cells. In some embodiments, the method includes differentiating a second portion of the progenitor cells to form mesenchymal cells. In some embodiments, the method includes co-culturing the epithelial cells and the mesenchymal cells in a mineral-stimulating media under conditions suitable to induce production of a mineralized material.

Another aspect is a method of forming a mineralized composition. In some embodiments, the method includes introducing epithelial cells into a matrix material. In some embodiments, the method includes introducing epithelial cells into the matrix material. In some embodiments, the method includes infusing a mineral-stimulating media into the matrix material. In some embodiments, the method includes co-culturing the epithelial cells and the mesenchymal cells in the mineral-stimulating media under conditions suitable to induce production of a mineralized material.

In some embodiments, the epithelial cells include ameloblasts. In some embodiments, the mesenchymal cells include osteoblasts or odontoblasts. In some embodiments, the epithelial cells comprise ameloblasts and the mesenchymal cells comprise osteoblasts or odontoblasts. In some embodiments, the progenitor cells comprise embryonic stem cells, umbilical cord stem cells, adult stem cells, dental stem cells, or induced pluripotent stem cells.

In some embodiments, the mineral-stimulating media includes an osteogenic media.

In some embodiments, the progenitor cells, epithelial cells, or mesenchymal cells, when present, are independently comprised of the matrix material at a density of from about 0.0001 million cells (M) ml$^{-1}$ up to about 1000 M ml$^{-1}$. In some embodiments, the ratio of epithelial cells and mesenchymal cells is about 100:1 to about 1:100.

In some embodiments, the co-culturing includes ex vivo co-culturing. In some embodiments, the co-culturing includes in vivo co-culturing. In some embodiments, the co-culturing includes ex vivo and in vivo co-culturing.

In some embodiments, the matrix includes a material selected from the group consisting of fibrin, fibrinogen, a collagen, a polyorthoester, a polyvinyl alcohol, a polyamide, a polycarbonate, a polyvinyl pyrrolidone, a marine adhesive protein, a cyanoacrylate, a polymeric hydrogel, and a combination thereof. In some embodiments, the matrix comprises at least one physical channel.

In some embodiments, the mineral-stimulating media includes amelogenin (e.g., naturally occurring or recombinant amelogenin) in an amount sufficient to increase nuclear translocalization of β-catenin, increase activation β-catenin, or increase accumulation of non-phosphorylated β-catenin. In some embodiments, amelogenin is cultured with one or more types of progenitor cells, epithelial cells, or mesenchymal cells so as to increase nuclear translocalization of β-catenin, increase activation β-catenin, or increase accumulation of non-phosphorylated β-catenin in such cells.

Another aspect provides a method of treating a mineralization-related tissue or organ defect. In some embodiments, the method includes grafting a composition described herein, or formed according to a method described herein, into a subject in need thereof.

Another aspect provides a method of increasing mineralization in a tissue or organ. In some embodiments, the method includes grafting a composition described herein, or formed according to a method described herein, into a subject in need thereof.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 1B, LS8—ameloblasts; FIG. 1C, 7F2—ATCC osteoblasts) or together (co-culture). Co-cultures with osteogenic media (OM) (FIG. 1D, SRE-G5+7F2; FIG. 1E, LS8+7F2) showed strong staining reaction compared with same cells in growth media (GM) (FIG. 1F, SRE-G5+7F2; FIG. 1G, LS8+7F2). Graphic shows relative quantization of AR-S staining (FIG. 1H).

FIG. 4A and FIG. 4B show odontoblast-like cells T4-4 and ameloblast like cells SRE-G5 co-cultures with osteogenic media (OM) and growth media (GM), respectively. FIG. 4C and FIG. 4D show co-cultures of T4-4 and ameloblast like cells LS8 with OM and GM, respectively. FIG. 4E shows alizarin red staining quantization by CPC destaining.

FIG. 5A is a bright field image, FIG. 5B is a fluorescence image, and FIG. 5C is an overlay of the bright field and fluorescence images. The GFP positive cells are osteoblast lineage cells.

FIG. 6B is a western blot confirming His-tagged amelogenin.

FIG. 7A-7G is a series of fluorescence microscopy images showing staining and a western blot showing levels of beta-catenin. FIG. 7A-C show beta-catenin fluorescent staining AML treated PDL cells. FIG. 7D-F shows beta-catenin fluorescent staining in untreated PDL cells. FIG. 7G is a western blot showing non-phosphorylated beta catenin levels.

FIG. 8A-8G is a series of fluorescence microscopy images showing staining and a western blot showing levels of beta-catenin in dental pulp cells. FIG. 8A-8C show beta-catenin fluorescent staining AML treated dental pulp cells. FIG. 8D-8F shows beta-catenin fluorescent staining in untreated dental pulp cells. FIG. 8G is a western blot showing non-phosphorylated beta catenin levels.

FIG. 9A shows the trend in PDL cells and FIG. 9B shows the trend in DPSC cells. The red and blue lines/points are AML-treated cells and untreated control cells, respectively.

FIG. 11A is a bar graph of RunX2 mRNA expression of Control (untreated), 1 μg AML-treated, and 5 μg AML-treated PDL cells. FIG. 11B is a bar graph of DSPP mRNA expression of Control (untreated), 1 μg AML-treated, and 5 μg AML-treated PDL cells. FIG. 11C shows RT-PCR data for RunX2 and DSPP expression confirmed by gel electrophoresis (2% agarose gel).

FIG. 13A is a series of images of DPSCs treated with 5 μg/ml AML, 1 μg/ml AML, and 0 μg/ml AML. FIG. 13B is a series of images of Van Kossa/ALP stained DPSCs treated with 5 μg/ml AML, 1 μg/ml AML, and 0 μg/ml AML. FIG. 13C is a bar graph of RunX2 mRNA expression of DPSCs treated with 5 μg/ml AML, 1 μg/ml AML, and 0 μg/ml AML at 2 and 3 weeks post-treatment. FIG. 13D is a bar graph of DSPP mRNA expression of DPSCs treated with 5 μg/ml AML, 1 μg/ml AML, and 0 μg/ml AML at 2 and 3 weeks post-treatment.

FIG. 14A is an image of C3H10t1/2 cells cultured in osteogenic medium treated with 0 μg/ml AML, 1 μg/ml AML, and 5 μg/ml AML. FIG. 14B-14C are images of AML-treated (5 μg/ml) (FIG. 14B) and untreated ALP and Van Kossa-stained C3H10t1/2 cells (FIG. 14C).

FIG. 15A is an image of C3H10t1/2 cells cultured in osteogenic medium treated with 0 μg/ml AML, 1 μg/ml AML, and 5 μg/ml AML. FIG. 15B is a series of images of untreated, 1 μg/ml AML-treated, and 5 μg/ml AML-treated ALP and Van Kossa-stained C3H10t1/2 cells. FIG. 15C is a bar graph of RunX2 mRNA expression in untreated and AML-treated C3H10t1/2 cells at 2 and 3 weeks.

FIG. 17A is a pair of Trichome-stained images of an untreated and 2-weeks, post-AML-treated PDL cell line to show the collagen matrix. FIG. 17B is a bar graph of the expression of Col1 mRNA in a control sample and an AML-treated sample of PDL cells. FIG. 17C is a series of images of ALP and Von Kossa stained PDL cells treated with 0, 1, and 5 µg/ml AML after two weeks in osteogenic medium. FIG. 17D-17F are a series of bar graphs of osteogenic differentiation cell markers (i.e., DSPP (FIG. 17D), DMP-1 (FIG. 17E), Osteocalcin (FIG. 17F), CEMP-1 (FIG. 17G)) in PDL cells treated with 0, 1, and 5 µg/ml AML after two weeks in osteogenic medium.

FIG. 18B is a fluorescence microscopy image showing nuclear translocalization. FIG. 18C is a bar graph showing Luciferase activity of untreated, amelogenin treated, and beta-catenin in human PDL cells. FIG. 18D is a bar graph showing LacZ activity in untreated, amelogenin-treated, BIO-treated, and Wnt3a-treated TOPGAL osteoblasts. FIG. 18E is a light microscopy image of LacZ stained sections in TOPGAL mice. FIG. 18F is an image of the same section in FIG. 18E, that is 6×His-tagged, shown as an overlap with the beta catenin signaling as indicated by the LacZ staining.

FIG. 19A is a series of Von Kossa-stained images 2 weeks after human PDL cells were transfected with the Wnt signal inhibitor, ICAT plasmid. FIG. 19B is an illustration of how the ICAT plasmid inhibits the Wnt signal. FIG. 19C-19D are bar graphs of DSPP and CEMP-1 expression of PDL cells treated (+) or untreated (−) with ICAT and AML.

FIG. 21A-21D is a series of images of PDL cells untreated, treated with amelogenin (5 µg/ml), BIO (1 µg/ml), or Wnt3A (50 ng/ml) 2 weeks post-treatment. FIG. 21E-G are bar graphs of expression of differentiation markers in human PDL cells untreated, treated with amelogenin (5 µg/ml), BIO (1 µg/ml), or Wnt3A (50 ng/ml) 2 weeks post-treatment.

FIG. 22A is a western blot confirming AML expression. FIG. 22B is a bar graph of marker gene expression of Osteocalcin, CEMP-1, and RunX2 differentiation markers. FIG. 22C is a pair of images of Von Kossa-stained human PDL cells.

FIG. 25A is a western blot confirming expression of AML. FIG. 25B-E are bar graphs of differentiation expression markers, DSPP, DMP-1, OPG, and RANKL in dental pulp cells transfected with AML in different culture environments (i.e., AML+osteogenic medium, AML+growth medium, Osteogenic medium, and growth medium) measured by RT-PCR.

FIG. 26 A-A" is a series of images of dental pulp cells transfected with AML in a scaffold. FIG. B-B" is a series of images of dental pulp cells in a scaffold (no AML). FIG. C-C' is a series of images of an empty scaffold.

FIG. 27 A-A" are images of AML stained sections of DSC cells treated with AML, DSC cells and scaffold, and DSC empty scaffold. FIG. 27 B-B" are images of DSP-stained sections of DSC cells treated with AML, DSC cells and scaffold, and DSC empty scaffold.

FIG. 29A is an image of AML-treated DSCs in osteogenic media. FIG. 29B is an image of AML-treated DSCs in growth media. FIG. 29C is an image of DSCs and vector in osteogenic media. FIG. 29D is an image of DSCs and vector in growth media.

DETAILED DESCRIPTION OF THE INVENTION

Figures 1A, 1B, 1C, 1D, 1E, 1F, 1G, 1H:
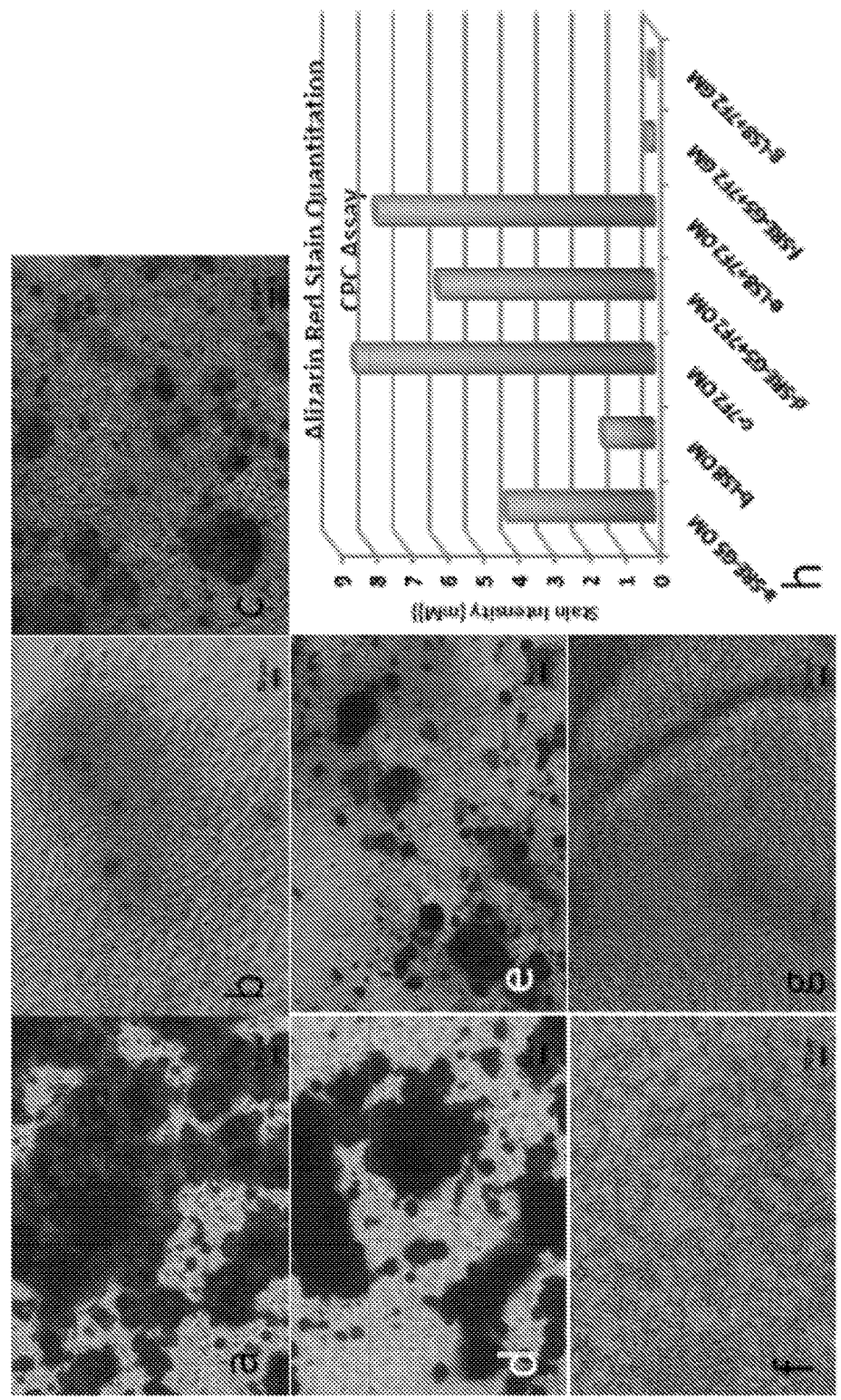
FIG. 1A-1H is a series of images of AR-S staining showing differential mineralization response between culturing cells alone (FIG. 1A, SRE-G5—ameloblasts.

The present disclosure is based, at least in party, on the observation that co-culture of ameloblasts (producers of enamel) and osteoblast/odontoblasts (producers of dentin) in a mineral-stimulating medium yielded robust in vitro mineralization (see e.g., Example 1). Such observations are based on at least Alizerin Red-S (calcium deposition) stain of cells cultured in various conditions, expression data of multiple ameloblast and odontoblast-related genes, and quantitative real-time PCR of these genes (see Example 1). As shown herein, expression of DMP1 and DSPP, along with ALP and amelogenin (see e.g., Example 1) supports use of the present system for bone regeneration and dentin regeneration.

Described herein is an approach for mass production of dental material, such as dentin and enamel, from progenitor cells, such as embryonic stem cells, umbilical cord stem cells, adult stem cells, and induced pluripotent stem cells. Various embodiments provide an process by which ameloblasts and osteoblasts/odontoblasts are co-cultured in chemically-defined, mineral-stimulating medium to produce mineralization. This approach yields more robust mineralization than these cells cultured separately or co-cultured in normal media. Thus is provided a mass production of enamel, dentin, and cementum for use in safer, more immunologically-compatible dental restorations.

While being under no obligation to provide a mechanistic explanation, and in no way limited the invention, it is presently thought that the co-culture system simulates epithelial-mesenchymal (e.g., ameloblast-osteoblast) interaction and thereby stimulates odontogenesis and osteogenesis. Thus is provided an approach to tailor epithelial-mesenchymal interactions for the regeneration of mineralized tissues including bone, dentin, cementum, and enamel structures.

Dental material produced according to approaches described herein can be useful for restoration of dentin, cementum and enamel in clinical settings, for example as filling materials for dental restorations. Dentin, cementum and enamel produced by cells have greater bio-compatibility than conventional materials, such as amalgam and composites, used for dental restoration. Dental products benefited by the source of dentin, cementum and enamel described herein include, but are not limited to, implants, bridges, crowns, and fillings.

The approach of growing cells in an artificial environment that closely mimics their native environment can provide higher yields of important compounds. A combination of scaffold and various cell types can provide for production of bone for use in, for example, bone grafts or joint replacements.

Progenitor Cells

In various embodiments, dental material, such as dentin, cementum and enamel, are produced from progenitor cells. In some embodiments, progenitor cells are differentiated to an epithelial cell and a mesenchymal, where such cells are then co-cultured to produce mineralization. For example, ameloblasts (an epithelial cell) and osteoblasts (a mesenchymal cell) can be co-cultured to produce mineralized materials.

A progenitor cell is a cell that is undifferentiated or partially undifferentiated, and can divide and proliferate to produce undifferentiated or partially undifferentiated cells or can differentiate to produce at least one differentiated or specialized cell. A progenitor cell can be a pluripotent cell, which means that the cell is capable of self-renewal and of trans-differentiation into multiple tissue types upon differentiation. Pluripotent progenitor cells include stem cells, such as embryonic stem cells and adult stem cells. A progenitor cell can be a multipotent cell. A progenitor cell can be self-renewing. For example, the progenitor cell can be a stem cell. As another example, the progenitor cell can be an adult stem cell. Examples of progenitor cells include, but are not limited to, embryonic stem cells, umbilical cord stem cells, adult stem cells, dental stem cells, and induced pluripotent stem cells.

Progenitor cells can be isolated, purified, or cultured by a variety of means known to the art. Methods for the isolation and culture of progenitor cells are discussed in, for example, Vunjak-Novakovic and Freshney (2006) Culture of Cells for Tissue Engineering, Wiley-Liss, ISBN-10 0471629359. A progenitor cell can be comprised of, or derived from, an animal, including, but not limited to, mammals, reptiles, and avians, more preferably horses, cows, dogs, cats, sheep, pigs, and chickens, and most preferably human.

As described herein, co-culture of epithelial cells (e.g., ameloblasts) and mesenchymal cells (e.g., osteoblasts or odontoblasts) in a mineral-stimulating media. In some embodiments, progenitor cells can differentiate into, or otherwise form, an epithelial cell or a mesenchymal cell. For example, progenitor cells can differentiate into, or otherwise form, ameloblasts, osteoblasts, or odontoblasts. Progenitor cells can be differentiated into epithelial cells (e.g., ameloblasts) and mesenchymal cells (e.g., osteoblasts or odontoblasts) by a variety of means known to the art.

Progenitor cells can include dental pulp stem cells or periodontal ligament stem cells. As shown herein, culture of dental pulp stem cells or periodontal ligament stem cells with amelogenin (e.g., recombinant amelogenin) showed increased ALP and Van Kossa staining, DSPP expression, β-catenin nuclear translocalization and activation, and accumulation of non-phosphorylated β-catenin. Thus, amelogenin can facilitate osteogenic and odontogenic lineage differentiation via upregulation of β-catenin. It is presently thought that amelogenin my enhance odontogenesis and osteogenesis by modulating the Wnt/beta-catenin signaling pathway.

Ameloblasts

In various embodiments, ameloblasts and osteoblasts/odontoblasts are co-cultured in chemically-defined, mineral-stimulating medium to produce mineralization. Ameloblasts are cells, present only during tooth development, that deposit tooth enamel. Ameloblast cells secrete the enamel proteins enamelin and amelogenin, which later mineralize to form enamel on teeth.

Ameloblasts are derived from oral epithelium tissue of ectodermal origin. Their differentiation from preameloblasts is a result of signaling from the ectomesenchymal cells of the dental papilla. An ameloblast generally becomes fully functional after the first layer of dentine has been formed by odontoblasts. The life cycle of an ameloblast generally includes: morphogenic stage, organizing stage, formative (secretory) stage, maturative stage, protective stage, and desmolytic stage.

Ameloblast cells can be isolated, purified, or cultured by a variety of means known to the art.

In various embodiments, amelogenin from culture methods described herein or recombinant production methods described herein, can be administered therapeutically according to its mineralization potential to promote odontogenesis and osteogenesis in tissue regeneration.

Amelogenin

Amelogenin is a protein product of ameloblasts in enamel formation and critical to the structure and mineralization of enamel in development. Amelogenin isoforms comprise ~90% of the mineralized matrix that covers the crown of the tooth bud. As amelogenin is cleaved and degraded, mineral deposition in the form of crystals takes place in a hierarchical pattern. During amelogenesis, an organic, protein-rich substance which comprises over 85% amelogenin is transformed into a completely mineralized architecture of hydroxyapatite of enamel.

Amelogenin can be naturally occurring amelogenin or recombinant amelogenin. Amelogenin can have a polypeptide sequence according to GenBank Accession No. AAB33093.1 (Mus sp.); GenBank Accession No. AAB29184.1 (human); GenBank Accession No. AAA51717.1 (human); GenBank Accession No. AAC21581.1 (human); Swiss-Prot Accession No. P45561.2 (pig); NCBI Accession No. NP_998965.1 (pig); GenBank Accession No. AAB03481.1 (rat); GenBank Accession No. AAB03483.1 (rat); GenBank Accession No. AAB03482.1 (rat); GenBank Accession No. AAB02691.1 (rat); GenBank Accession No. AAB06753.1 (rat); NCBI Accession No. NP_001166340.1 (guinea pig); GenBank Accession No. CAA09957.1 (guinea pig); GenBank Accession No. AAB23270.2 (cow); GenBank Accession No. AAA30373.1 (cow); GenBank Accession No. AAA30372.1 (cow); GenBank Accession No. AA30371.1 (cow); GenBank Accession No. AAC78135.1 (frog); GenBank Accession No. AAC78134.1 (frog); or GenBank Accession No. AAC78133.1 (caiman); or a polypeptide sequence having at least about 85%, at least about 90%, at least about 91%, at least about 92%, at least about 93%, at least about 94%, at least about 95%, at least about 96%, at least about 97%, at least about 98%, or at least about 99% sequence identity thereto and retaining substantial activity associated with amelogenin.

Recombinant amelogenin can be produced according to methods described herein (see e.g., Examples 4-5).

As shown herein, culture of dental pulp stem cells or periodontal ligament stem cells with amelogenin (e.g., recombinant amelogenin) showed increased ALP and Van Kossa staining, DSPP expression, β-catenin nuclear translocalization and activation, and accumulation of non-phosphorylated β-catenin. Thus, amelogenin can facilitate osteogenic and odontogenic lineage differentiation via upregulation of β-catenin. It is presently thought that amelogenin my enhance odontogenesis and osteogenesis by modulating the Wnt/beta-catenin signaling pathway.

Osteoblast and Odontoblast-Like Cells

In various embodiments, osteoblasts/odontoblasts and ameloblasts are co-cultured in chemically-defined, mineral-stimulating medium to produce mineralization.

Osteoblasts are mononucleate cells responsible for bone formation. Osteoblasts arise from osteoprogenitor cells located in the periosteum and the bone marrow. Once osteoprogenitors start to differentiate into osteoblasts, they begin to express a range of genetic markers including Osterix, Col1, BSP, M-CSF, ALP, osteocalcin, osteopontin, and osteonectin. Osteoblast cells can be isolated, purified, or cultured by a variety of means known to the art.

An odontoblast is a biological cell of neural crest origin that is part of the outer surface of the dental pulp, and whose biological function is dentinogenesis, which is the creation of dentin, the substance under the tooth enamel. Odontoblast cells can be isolated, purified, or cultured by a variety of means known to the art.

Mineral-Stimulating Media

In various embodiments, epithelial cells (e.g., ameloblasts) and mesenchymal cells (e.g., osteoblasts or odontoblasts) are co-cultured in a mineral-stimulating medium to produce mineralized materials. A variety of media for stimulating mineralization are known in the art. For example, a media for stimulating mineralization can include an osteogenic media (see Example 1). An osteogenic media can be according to a commercially available osteogenic media (e.g., StemXVivo™, R&D Systems; StemPro Osteogenesis Differentiation Kit, Invitrogen; OST.D.Media-450, BlossomBIO, Gentaur Molecular Products; HyClone Osteogenic Differentiation Kit, Thermo Scientific; Osteogenic Differentiation Media, Tebu-Bio).

Scaffold and Matrix Material

Various embodiments of the compositions and methods described herein employ a scaffold seeded with progenitor cells, epithelial cells, mesenchymal cells, or a combination thereof. As described herein, co-culturing of epithelial cells (e.g., ameloblasts) and mesenchymal cells (e.g., osteoblasts or odontoblasts) with mineral-stimulating medium can result in the production of mineralized materials. Where cells are co-cultured in a scaffold, the mineralized materials can likewise be produced in or on the scaffold. Accordingly, the shape and characteristics of the scaffold can be chosen so as to provide a desired framework for the mineralized materials.

A scaffold can be fabricated with any matrix material recognized as useful by the skilled artisan. A matrix material can be a biocompatible material that generally forms a porous, microcellular scaffold, which provides a physical support for cells migrating thereto. Such matrix materials can: allow cell attachment and migration; deliver and retain cells and biochemical factors; enable diffusion of cell nutrients and expressed products; or exert certain mechanical and biological influences to modify the behavior of the cell phase. The matrix material generally forms a porous, microcellular scaffold of a biocompatible material that provides a physical support and an adhesive substrate for growth of cells during in vitro or in vivo culturing.

The matrix comprising the scaffold can have an adequate porosity and an adequate pore size so as to facilitate cell growth and diffusion throughout the whole structure of both cells and nutrients. The matrix can be biodegradable providing for absorption of the matrix by the surrounding tissues (if implanted), which can eliminate the necessity of a surgical removal. The rate at which degradation occurs can coincide as much as possible with the rate of tissue or organ formation. Thus, while cells are fabricating their own natural structure around themselves (e.g., dentin, cementum, enamel), the matrix is able to provide structural integrity and eventually break down, leaving the neotissue, newly formed tissue or organ which can assume the mechanical load. The matrix can be an injectable matrix in some configurations. The matrix can be delivered to a tissue using minimally invasive endoscopic procedures.

The scaffold can comprise a matrix material having different phases of viscosity. For example, a matrix can have a substantially liquid phase or a substantially gelled phase. The transition between phases can be stimulated by a variety of factors including, but limited to, light, chemical, magnetic, electrical, and mechanical stimulus. For example, the matrix can be a thermosensitive matrix with a substantially liquid phase at about room temperature and a substantially gelled phase at about body temperature. The liquid phase of the matrix can have a lower viscosity that provides for optimal distribution of growth factors or other additives and injectability, while the solid phase of the matrix can have an elevated viscosity that provides for matrix retention at or within the target tissue.

The scaffold can comprise a matrix material formed of synthetic polymers. Such synthetic polymers include, but are not limited to, polyurethanes, polyorthoesters, polyvinyl alcohol, polyamides, polycarbonates, polyvinyl pyrrolidone, marine adhesive proteins, cyanoacrylates, analogs, mixtures, combinations and derivatives of the above. Alternatively, the matrix can be formed of naturally occurring biopolymers. Such naturally occurring biopolymers include, but are not limited to, fibrin, fibrinogen, fibronectin, collagen, and other suitable biopolymers. Also, the matrix can be formed from a mixture of naturally occurring biopolymers and synthetic polymers.

The scaffold can include one or more matrix materials including, but not limited to, a collagen gel, a polyvinyl alcohol sponge, a poly(D,L-lactide-co-glycolide) fiber matrix, a polyglactin fiber, a calcium alginate gel, a polyglycolic acid mesh, polyester (e.g., poly-(L-lactic acid) or a polyanhydride), a polysaccharide (e.g. alginate), polyphosphazene, polyacrylate, or a polyethylene oxide-polypropylene glycol block copolymer. Matrices can be produced from proteins (e.g. extracellular matrix proteins such as fibrin, collagen, and fibronectin), polymers (e.g., polyvinylpyrrolidone), or hyaluronic acid. Synthetic polymers can also be used, including bioerodible polymers (e.g., poly(lactide), poly(glycolic acid), poly(lactide-co-glycolide), poly(caprolactone), polycarbonates, polyamides, polyanhydrides, polyamino acids, polyortho esters, polyacetals, polycyanoacrylates), degradable polyurethanes, non-erodible polymers (e.g., polyacrylates, ethylene-vinyl acetate polymers and other acyl substituted cellulose acetates and derivatives thereof), non-erodible polyurethanes, polystyrenes, polyvinyl chloride, polyvinyl fluoride, poly(vinylimidazole), chlorosulphonated polyolifins, polyethylene oxide, polyvinyl alcohol, Teflon®, or nylon.

The scaffold can further comprise any other bioactive molecule, for example an antibiotic or an additional chemotactic growth factor or another osteogenic, dentinogenic, amelogenic, or cementogenic growth factor. In some embodiments, the scaffold is strengthened, through the addition of, e.g., human serum albumin (HSA), hydroxyethyl starch, dextran, or combinations thereof. Suitable concentrations of these compounds for use in the compositions of the application are known to those of skill in the art, or can be readily ascertained without undue experimentation. The concentration of compound in the scaffold will vary with the nature of the compound, its physiological role, and desired therapeutic or diagnostic effect. A therapeutically effective amount is generally a sufficient concentration of therapeutic agent to display the desired effect without undue toxicity. The compound can be incorporated into the scaffold or matrix material by any known method. In some embodiments, the compound is imbedded in a gel, e.g., a collagen gel incorporated into the pores of the scaffold or matrix material.

Alternatively, chemical modification methods can be used to covalently link the compound to a matrix material. The surface functional groups of the matrix can be coupled with reactive functional groups of the compound to form covalent bonds using coupling agents well known in the art such as aldehyde compounds, carbodiimides, and the like. Additionally, a spacer molecule can be used to gap the surface reactive groups and the reactive groups of the biomolecules to allow more flexibility of such molecules on the surface of the matrix. Other similar methods of attaching biomolecules to the interior or exterior of a matrix will be known to one of skill in the art.

Pores and channels of the scaffold can be engineered to be of various diameters. For example, the pores of the scaffold can have a diameter range from micrometers to millimeters. In some embodiments, the pores of the matrix material include microchannels. Microchannels generally have an average diameter of about 0.1 µm to about 1,000 µm, e.g., about 50 µm to about 500 µm (for example about 100 µm, 150 µm, about 200 µm, about 250 µm, about 300 µm, about 350 µm, about 400 µm, about 450 µm, about 500 µm, or about 550 µm). One skilled in the art will understand that the distribution of microchannel diameters can have any distribution including a normal distribution or a non-normal distribution. In some embodiments, microchannels are a naturally occurring feature of the matrix material(s). In other embodiments, microchannels are engineered to occur in the matrix materials.

Several methods can be used for fabrication of porous scaffolds, including particulate leaching, gas foaming, electrospinning, freeze drying, foaming of ceramic from slurry, and the formation of polymeric sponge. Other methods can be used for fabrication of porous scaffolds include computer aided design (CAD) and synthesizing the scaffold with a bioplotter (e.g., solid freeform fabrication) (e.g., Bioplotter™, EnvisionTec, Germany).

Biologic drugs that can be added to the compositions of the invention include immunomodulators and other biological response modifiers. A biological response modifier generally encompasses a biomolecule (e.g., peptide, peptide fragment, polysaccharide, lipid, antibody) that is involved in modifying a biological response, such as the immune response or tissue or organ growth and repair, in a manner that enhances a particular desired therapeutic effect, for example, the cytolysis of bacterial cells or the growth of tissue- or organ-specific cells or vascularization. Biologic drugs can also be incorporated directly into the matrix component. Those of skill in the art will know, or can readily ascertain, other substances which can act as suitable non-biologic and biologic drugs.

Compositions described herein can also be modified to incorporate a diagnostic agent, such as a radiopaque agent. Such compounds include barium sulfate as well as various organic compounds containing iodine. Examples of these latter compounds include iocetamic acid, iodipamide, iodoxamate meglumine, iopanoic acid, as well as diatrizoate derivatives, such as diatrizoate sodium. Other contrast agents that can be utilized in the compositions of the invention can be readily ascertained by those of skill in the art and can include, for example, the use of radiolabeled fatty acids or analogs thereof.

The concentration of an agent in the composition will vary with the nature of the compound, its physiological role, and desired therapeutic or diagnostic effect. A therapeutically effective amount is generally a sufficient concentration of therapeutic agent to display the desired effect without undue toxicity. A diagnostically effective amount is generally a concentration of diagnostic agent which is effective in allowing the monitoring of the integration of the tissue graft, while minimizing potential toxicity. In any event, the desired concentration in a particular instance for a particular compound is readily ascertainable by one of skill in the art.

Infusion and Culturing

In various embodiments, cells are introduced (e.g., implanted, injected, infused, or seeded) into or onto an artificial structure (e.g., a scaffold comprising a matrix material) capable of supporting three-dimensional tissue or organ formation. For example, progenitor cells can be introduced into a scaffold, induced to differentiate into epithelial cells and mesenchymal cells, where such cells are then co-cultured within the scaffold under conditions suitable for production of mineralized materials. As another example, epithelial cells and mesenchymal cells can be introduced into a scaffold, where they are co-cultured under conditions suitable for production of mineralized materials. As another example, ameloblasts and osteoblasts or odontoblasts can be introduced into a scaffold, where they are co-cultured under conditions suitable for production of mineralized materials.

Cells of different types can be co-introduced or sequentially introduced. Cells of different types can be introduced in the same spatial position, similar spatial positions, or different spatial positions, relative to each other. It is contemplated that more than one of progenitor cells, epithelial cells, mesenchymal cells, ameloblasts, osteoblasts, or odontoblasts, including in different combinations, can be introduced into the matrix.

Cells of types described above can be introduced into the matrix material by a variety of means known to the art. Methods for the introduction (e.g., infusion, seeding, injection, etc.) of progenitor cells into or into the matrix material are discussed in, for example, Ma and Elisseeff, ed. (2005)

Scaffolding In Tissue Engineering, CRC, ISBN 1574445219; Saltzman (2004) Tissue Engineering: Engineering Principles for the Design of Replacement Organs and Tissues, Oxford ISBN 019514130X; Minuth et al. (2005) Tissue Engineering: From Cell Biology to Artificial Organs, John Wiley & Sons, ISBN 3527311866. For example, progenitor cells can be introduced into or onto the matrix by methods including hydrating freeze-dried scaffolds with a cell suspension (e.g., at a concentration of 100 cells/ml to several million cells/ml). Methods of addition of additional agents vary, as discussed below.

Methods of culturing and differentiating progenitor cells in or on scaffolds are generally known in the art (see e.g., Saltzman (2004) Tissue Engineering: Engineering Principles for the Design of Replacement Organs and Tissues, Oxford ISBN 019514130X; Vunjak-Novakovic and Freshney, eds. (2006) Culture of Cells for Tissue Engineering, Wiley-Liss, ISBN 0471629359; Minuth et al. (2005) Tissue Engineering: From Cell Biology to Artificial Organs, John Wiley & Sons, ISBN 3527311866). Incubation (and subsequent replication and/or differentiation) of the engineered composition containing co-cultured cell types in or on the matrix material can be, for example, at least in part in vitro, substantially in vitro, at least in part in vivo, or substantially in vivo. Determination of optimal culture time is within the skill of the art. A suitable medium can be used for in vitro progenitor cell infusion, differentiation, or cell transdifferentiation (see e.g., Vunjak-Novakovic and Freshney, eds. (2006) Culture of Cells for Tissue Engineering, Wiley-Liss, ISBN 0471629359; Minuth et al. (2005) Tissue Engineering: From Cell Biology to Artificial Organs, John Wiley & Sons, ISBN 3527311866). The culture time can vary from about an hour, several hours, a day, several days, a week, or several weeks. The quantity and type of cells present in the matrix can be characterized by, for example, morphology by ELISA, by protein assays, by genetic assays, by mechanical analysis, by RT-PCR, and/or by immunostaining to screen for cell-type-specific markers (see e.g., Minuth et al. (2005) Tissue Engineering: From Cell Biology to Artificial Organs, John Wiley & Sons, ISBN 3527311866).

The present disclosure includes methods for optimizing the density of both epithelial cells (e.g., ameloblasts) and mesenchymal cells (e.g., osteoblasts or odontoblasts) (and their lineage derivatives) so as to maximize mineralization production. Cell densities in a matrix can be monitored over time and at end-points. Tissue properties can be determined, for example, using standard techniques known to skilled artisans, such as histology, structural analysis, immunohistochemistry, biochemical analysis, and mechanical properties. As will be recognized by one skilled in the art, the cell densities of epithelial cells and mesenchymal cells can vary according to, for example, progenitor type, tissue or organ type, matrix material, matrix volume, infusion method, seeding pattern, culture medium, growth factors, incubation time, incubation conditions, and the like. Generally, for both epithelial cells and mesenchymal cells, the cell density of each cell type in a matrix can be, independently, from 0.0001 million cells (M) $ml^{-1}$ to about 1000 M $ml^{-1}$. For example, the epithelial cells and mesenchymal cells can each be present in the matrix at a density of about 0.001 M $ml^{-1}$, 0.01 M $ml^{-1}$, 0.1 M $ml^{-1}$, 1 M $ml^{-1}$, 5 M $ml^{-1}$, 10 M $ml^{-1}$, 15 M $ml^{-1}$, 20 M $ml^{-1}$, 25 M $ml^{-1}$, 30 M $ml^{-1}$, 35 M $ml^{-1}$, 40 M $ml^{-1}$, 45 M $ml^{-1}$, 50 M $ml^{-1}$, 55 M $ml^{-1}$, 60 M $ml^{-1}$, 65 M $ml^{-1}$, 70 M $ml^{-1}$, 75 M $ml^{-1}$, 80 M $ml^{-1}$, 85 M $ml^{-1}$, 90 M $ml^{-1}$, 95 M $ml^{-1}$, 100 M $ml^{-1}$, 200 M $ml^{-1}$, 300 M $ml^{-1}$, 400 M $ml^{-1}$, 500 M $ml^{-1}$, 600 M $ml^{-1}$, 700 M $ml^{-1}$, 800 M $ml^{-1}$, or 900 M $ml^{-1}$.

Epithelial cells and mesenchymal cells can be introduced at various ratios in or on the matrix. As will be recognized by one skilled in the art, the cell ratio of epithelial cells and mesenchymal cells can vary according to, for example, type of progenitor cells, target tissue or organ type, matrix material, matrix volume, infusion method, seeding pattern, culture medium, growth factors, incubation time, and/or incubation conditions. Generally, the ratio of epithelial cells and mesenchymal cells can be about 100:1 to about 1:100. For example, the ratio of epithelial cells and mesenchymal cells can be about 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20.

Therapeutic Methods

Also provided is a process of treating a mineralization injury, disease or disorder in a subject in need administration of a therapeutically effective amount of composition or construct described herein, so as to increase mineralization in a target structure, tissue, or organ. The mineralized compositions and constructs described herein hold significant clinical value because mineralized materials such as enamel, dentin, and cementum are safer, more immunologically-compatible materials for dental restorations.

A determination of the need for treatment will typically be assessed by a history and physical exam consistent with the structure, tissue or organ defect at issue. Subjects with an identified need of therapy include those with a diagnosed mineralized structure, tissue or organ defect. As an example, a defect may include bone fracture, tooth extraction sockets, periodontal defects, non-unions, dental and orthopedic implant integration, and bony augmentation in reconstructive and plastic procedures. The subject is preferably an animal, including, but not limited to, mammals, reptiles, and avians, more preferably horses, cows, dogs, cats, sheep, pigs, and chickens, and most preferably human.

As an example, a subject in need may have a mineralized deficiency of at least 5%, 10%, 25%, 50%, 75%, 90% or more of a particular structure, tissue, or organ. As another example, a subject in need may have damage to a mineralized structure of a tissue or organ, and the method provides an increase in biological function by at least 5%, 10%, 25%, 50%, 75%, 90%, 100%, or 200%, or even by as much as 300%, 400%, or 500%. As yet another example, the subject in need may have a mineralization-related disease, disorder, or condition, and the method provides a mineralized engineered tissue or organ construct sufficient to ameliorate or stabilize the disease, disorder, or condition. In a further example, the subject in need may have an increased risk of developing a mineralization-related disease, disorder, or condition that is delayed or prevented by the method.

Implantation of a mineralized or mineralizable engineered tissue or organ construct is within the skill of the art. The matrix and cellular assembly can be either fully or partially implanted into a tissue or organ of the subject to become a functioning part thereof. The implant can initially attach to and communicate with the host through a cellular monolayer. Over time, the introduced cells can expand and migrate out of the polymeric matrix to the surrounding tissue. After implantation, cells surrounding the engineered vascularized tissue composition can enter through cell migration. The cells surrounding the engineered tissue can be attracted by biologically active materials, including biological response modifiers, such as polysaccharides, proteins, peptides, genes, antigens, and antibodies which can be selectively incorporated into the matrix to provide the needed selectivity, for example, to tether the cell receptors to the matrix or stimulate cell migration into the matrix, or both. Generally, the matrix is porous, having interconnecting microchannels and/or macrochannels that allow for cell migration, augmented by both biological and physical-chemical gradients. For example, cells surrounding the implanted matrix can be attracted by biologically active materials including one ore more of VEGF, fibroblast growth factor, transforming growth factor-beta, endothelial cell growth factor, P-selectin, and intercellular adhesion molecule. One of skill in the art will recognize and know how to use other biologically active materials that are appropriate for attracting cells to the matrix.

Molecular Engineering

Design, generation, and testing of the variant nucleotides, and their encoded polypeptides, having the above required percent identities and retaining a required activity of the expressed protein is within the skill of the art. For example, directed evolution and rapid isolation of mutants can be according to methods described in references including, but not limited to, Link et al. (2007) Nature Reviews 5 (9), 680-688; Sanger et al. (1991) Gene 97 (1), 119-123; Ghadessy et al. (2001) Proc Natl Acad Sci USA 98 (8) 4552-4557. Thus, one skilled in the art could generate a large number of nucleotide and/or polypeptide variants having, for example, at least 95-99% identity to the reference sequence described herein and screen such for desired phenotypes according to methods routine in the art. Generally, conservative substitutions can be made at any position so long as the required activity is retained.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m=81.5°$ C.$+16.6(\log_{10}[Na^+])+0.41$(fraction G/C content)$-0.63$(% formamide)$-(600/l)$. Furthermore, the $T_m$ of a DNA:DNA hybrid is decreased by 1-1.5° C. for every 1% decrease in nucleotide identity (see e.g., Sambrook and Russel, 2006).

Host cells can be transformed using a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Host strains developed according to the approaches described herein can be evaluated by a number of means known in the art (see e.g., Studier (2005) Protein Expr Purif. 41 (1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Methods of down-regulation or silencing genes are known in the art. For example, expressed protein activity can be down-regulated or eliminated using antisense oligonucleotides, protein aptamers, nucleotide aptamers, and RNA interference (RNAi) (e.g., small interfering RNAs (sRNA), short hairpin RNA (shRNA), and micro RNAs (miRNA) (see e.g., Fanning and Symonds (2006) Handb Exp Pharmacol. 173, 289-303G, describing hammerhead ribozymes and small hairpin RNA; Helene, C., et al. (1992) Ann. N.Y. Acad. Sci. 660, 27-36; Maher (1992) Bioassays 14 (12): 807-15, describing targeting deoxyribonucleotide sequences; Lee et al. (2006) Curr Opin Chem Biol. 10, 1-8, describing aptamers; Reynolds et al. (2004) Nature Biotechnology 22 (3), 326-330, describing RNAi; Pushparaj and Melendez (2006) Clinical and Experimental Pharmacology and Physiology 33 (5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, TX; Sigma Aldrich, MO; Invitrogen). Several sRNA molecule design programs using a variety of algorithms are known to the art (see e.g., Cenix algorithm, Ambion; BLOCK-iT™ RNAi Designer, Invitrogen; sRNA Whitehead Institute Design Tools, Bioinofrmatics & Research Computing). Traits influential in defining optimal sRNA sequences include G/C content at the termini of the siRNAs, Tm of specific internal domains of the sRNA, sRNA length, position of the target sequence within the CDS (coding region), and nucleotide content of the 3' overhangs.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to progenitor cells, ameloblasts, epithelial cells, mesenchymal cells, osteoblasts, odontoblasts, differentiation media, mineral-stimulating media, scaffolds, matrix materials, and various combinations thereof. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Definitions and methods described herein are provided to better define the present invention and to guide those of ordinary skill in the art in the practice of the present invention. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the invention are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present invention.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

This example provides a co-culture system that stimulates mineral apposition by ameloblast-like cells and osteoblast/odontoblast-like cells in an approach that is thought to simulate epithelial-mesenchymal interaction. Experiments were designed to show interaction between ameloblast (epithelial) and osteoblast (mesenchymal) during co-culture.

Two ameloblast cell lines (LS8 and SRE-G5) and an odontoblast/osteoblast-cell line (7F2, ATCC) were co-cultured in chemically defined, mineral-stimulating medium (osteogenic media, OM) (StemPro Osteogenesis Differentiation Kit, Invitrogen, Carlsbad, Calif.). SRE-G5 cells were established dental epithelium-derived clones from 6-day-old rat incisors the largest producers of amelogenin mRNA (Abe et al. 2007 J Biosci Bioeng 103 (5), 479-485).

The same cells were co-cultured in non-differentiation growth medium as control groups. In the control group, growth media (GM) for each cell (for 7F2+LS8 DMEM with 10% FBS and for 7F2+SRE-G5 DMEM/F12 with 10% FBS) were used.

LS8 cells, the mouse enamel organ epithelial cell line, is an immortalized ameloblast-like cell line that expresses enamel-specific genes such as amelogenin and ameloblastin (Chen et al. 1992 Arch Oral Biol 37 (10), 771-778). There are no published data regarding LS8 and SRE-G5 mineralization. Huang et al. (Huang et al. 2008 J Bone Miner Res 23 (12), 1995-2006) used bioactive nanofibers and showed very mild mineralization response with LS8 cells. There was no attempt to use SRE-G5 cells for enamel matrix regeneration.

Since 7F2 osteoblast cell lines (ATTC) represents mature osteoblast cells we would like to see if the interaction between ameloblast (epithelial) and osteoblast (mesenchymal) cell in terms of co-culturing.

Following 3 weeks, Alizerin Red-S (AR-S) staining was used as an indicator for calcium deposition. AR-S concentration was determined by absorbance with a quantitative destaining procedure using 10% (w/v) cetylpyridinium chloride (CPC). Typically AR-S dye binds selectively 2 mol of $Ca^{2+}$/mol of dye in solution. In brief, cultures were rinsed with PBS, fixed by 4% formalin, rinsed three times and stained for 1 min with 40 mM AR-S. Thereafter cultures were rinsed again three times with distilled water. Destaining was performed with 10% (w/v) cetylpyridinium chloride (CPC) in 10 mM sodium phosphate for 15 min at room temperature. Aliquots of AR-S extracts were diluted 10 fold and AR-S concentration determined by absorbance measurement at 562 nm using AR-S standard curve in the same solution. Values were normalized by standard curve (Stanford et al. 1995 J Biol Chem 270 (16), 9420-9428).

Co-cultured cells growing on coverslips were washed twice in rinse buffer and fixed with 10% formaldehyde and single immunofluorescent (IF) labeling technique was performed using antibodies raised against DSPP, DMP-1, amelogenin and ALP. FTIR microspectroscopy examinations were also performed.

Quantitative real time RT-PCR analyses were used to evaluate 8 ameloblast and 2 odontoblast-related target genes expressions between groups. ODAM (Odontogenic ameloblast-associated protein) plays a role in enamel mineralization through the regulation of MMP-20 and Runx2. Amelotin is an enamel matrix protein expressed at the secretion and maturation stages of enamel development. MMP20 is a tooth-specific matrix metalloproteinase that is expressed during the early through middle stages of enamel development. Tuftelin is enamel glycoprotein: potential initialization of enamelization. Dentin Matrix Acidic Protein (DMP1) orchestrates mineralization matrix formation Results showed that AR-S-positive mineralization nodules first appeared around day 7 and gradually increased in diameter (see e.g., FIG. 1).

Figures 2A, 2B, 2C, 2D:
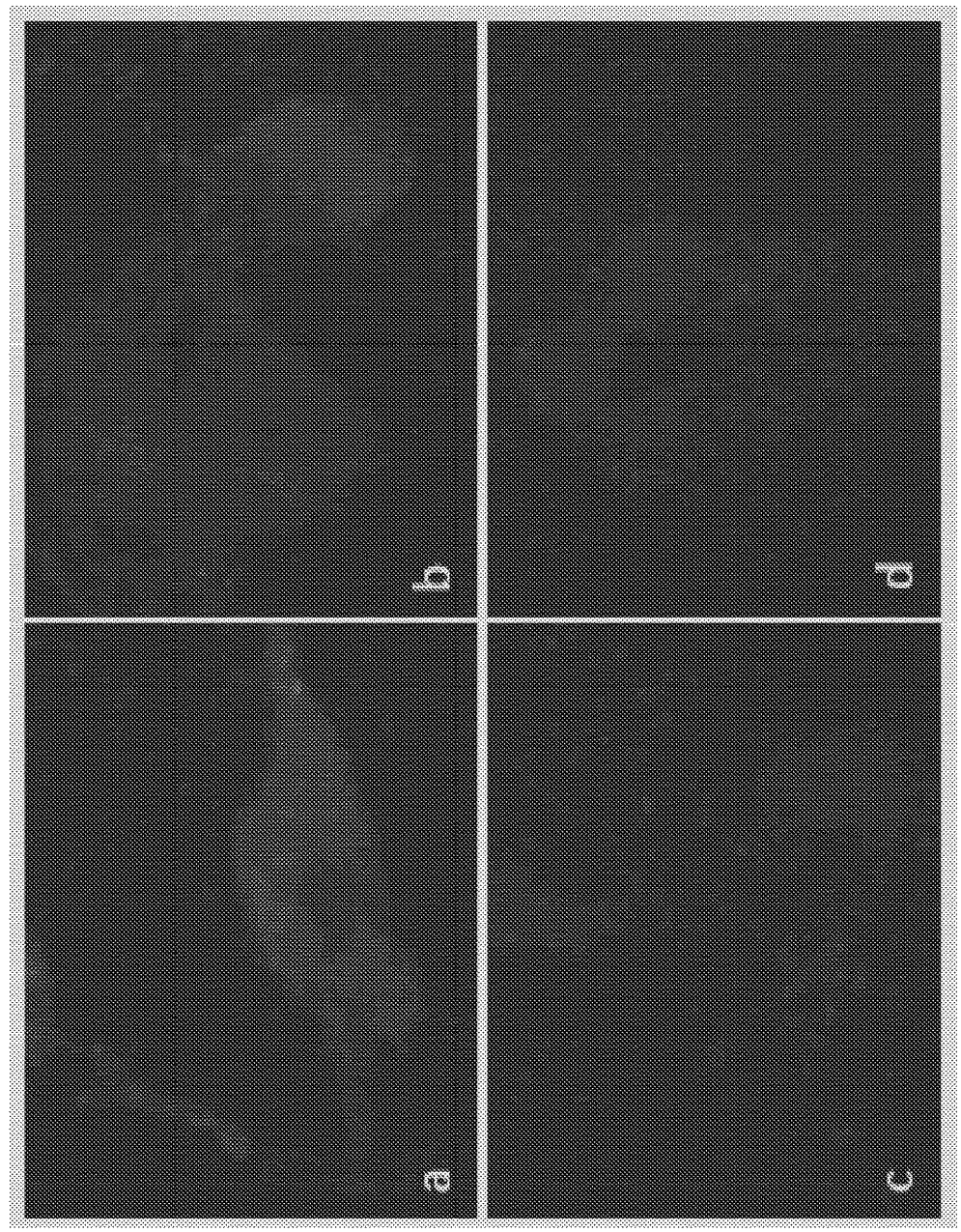
FIG. 2A-2D is a series of images showing that, after 1-wk co-culture, LS8+7F2 (ameloblasts+odontoblasts/osteoblasts) expressed strong ALP (FIG. 2A), DMP1 (FIG. 2B); DSPP (FIG. 2C) and amelogenin (FIG. 2D) although D and P staining is weak.
Figure 3A:
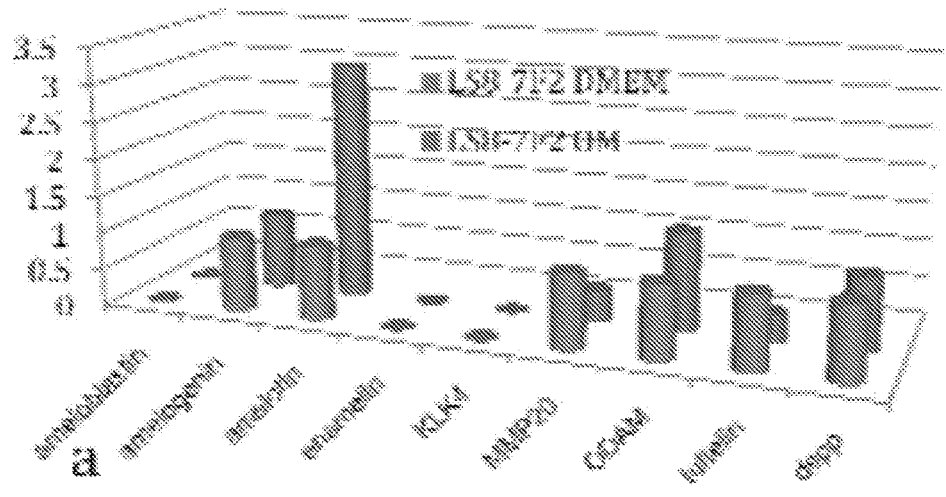
FIG. 3A-3B is a series of bar graphs showing upregulated expression of target genes according to quantitative real-time PCR. Values were normalized to LS8+7F2 GM group.
Figure 3B:
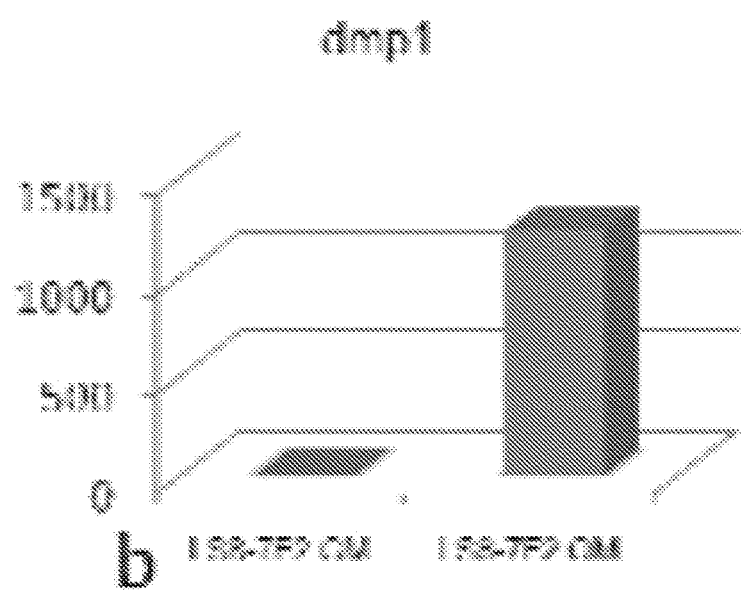

The IF study revealed co-cultured LS8+7F2 cells contributing to the nodule formation strongly express ALP, moderately express DMP1, and weakly express DSPP and amelogenin (see e.g., FIG. 2). The composition of the nodules was also analyzed by FTIR infrared microspectroscopy and spectra showed a weak analogy between two groups indicating different mineralization patterns.

qRT-PCR also confirmed those results showing higher expression of amelogenetic and odonto/osteogenetic markers in LS8+7F2 co-culture group.

Thus, co-culture of ameloblasts and osteoblast/odontoblasts yielded both the molecular and the mineral characteristics of the mineralized matrix.

Example 2

This example shows images of ameloblast cell lines co-cultured in OM or GM along with Alizarin Red stain intensity for each culture environment.

Two ameloblast cell lines (LS8 and SRE-G5) and an odontoblast/osteoblast-cell line (T4-4) were co-cultured in OM or GM. Alzarin Red stain intensity was measured for each culturing method.

Figures 4A, 4B, 4C, 4D:
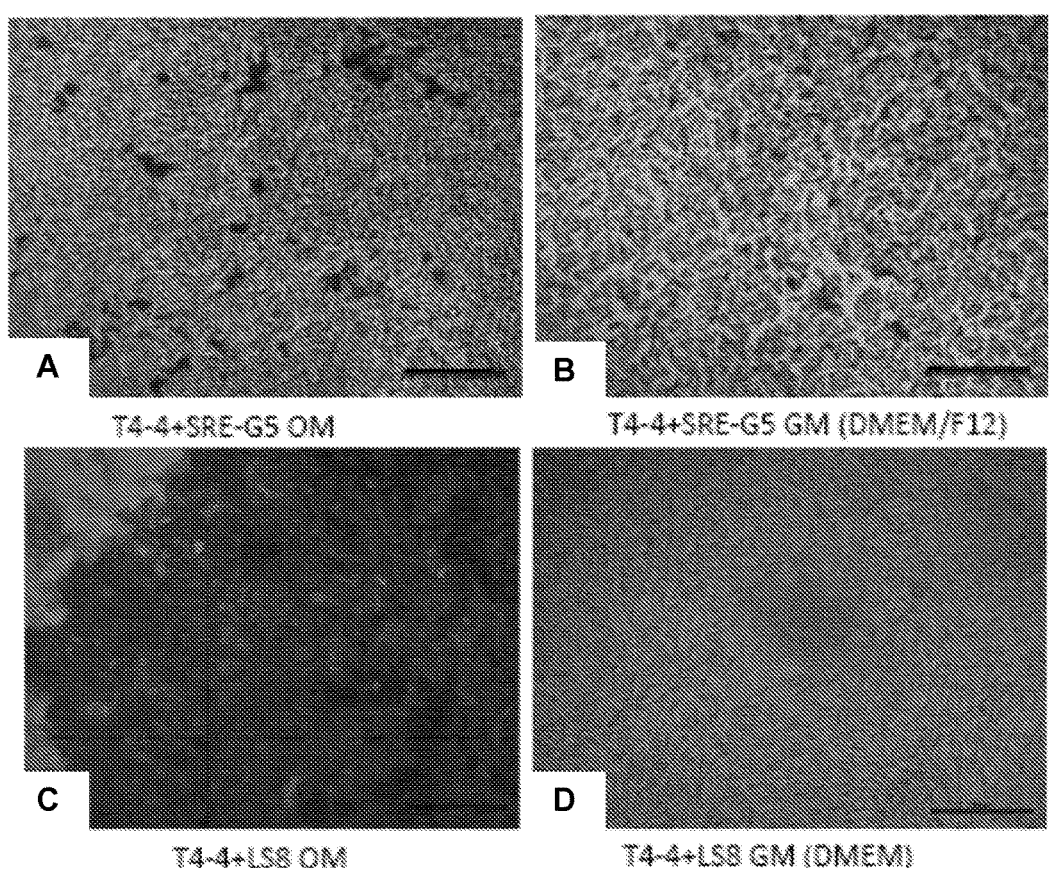
FIG. 4A-4E is a series of images and a bar graph showing mineralization response in T4-4 cells co-cultured with SRE-G5 cells (T4-4+SRE-G5) or T4-4 cells co-cultured with LS8 cells (T4-4+LS8) in osteogenic media (OM) or growth media (GM). AR-S staining showed differential mineralization response between different co-cultures.
Figure 4E:
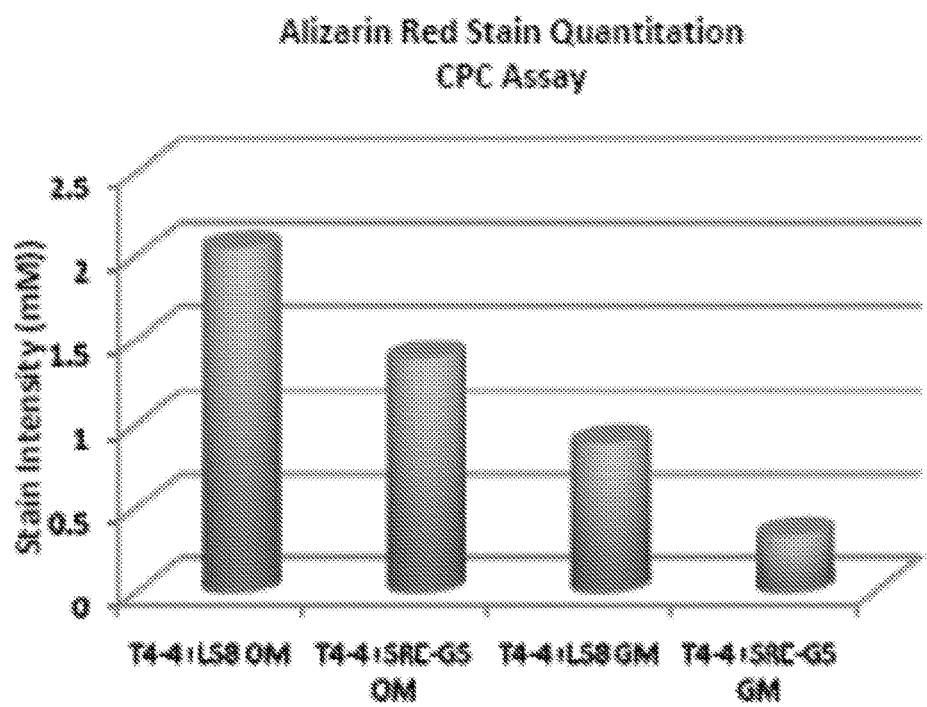

Representative results are shown in FIG. 4.

Example 3

Figure 5A:
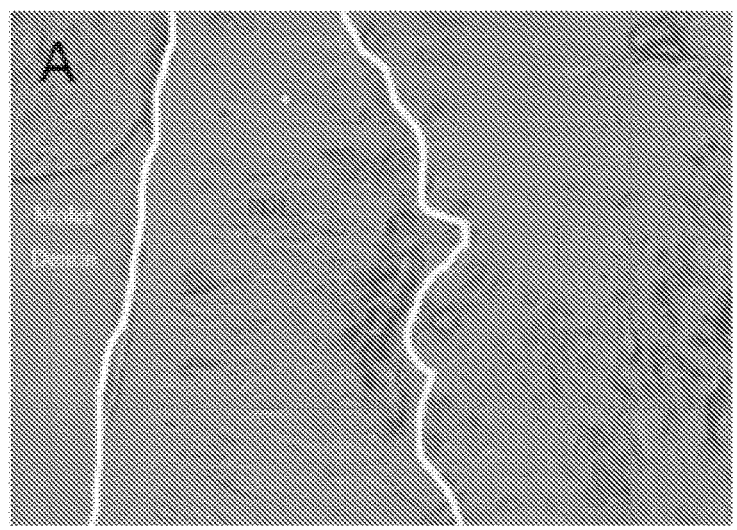
FIG. 5A-5C is a series of images from a section of a sample from a Col1a1 (2.3 kb)-Cre mouse crossed with Rosa26R mouse.
Figure 5B:
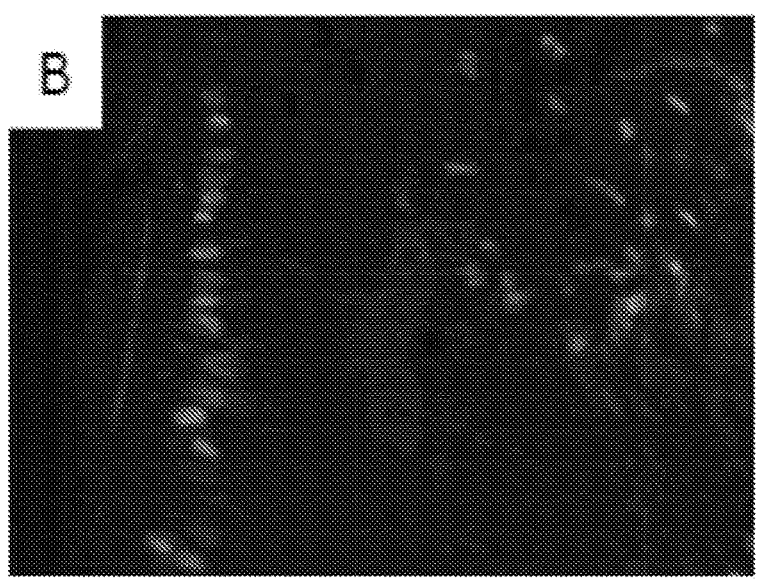
Figure 5C:
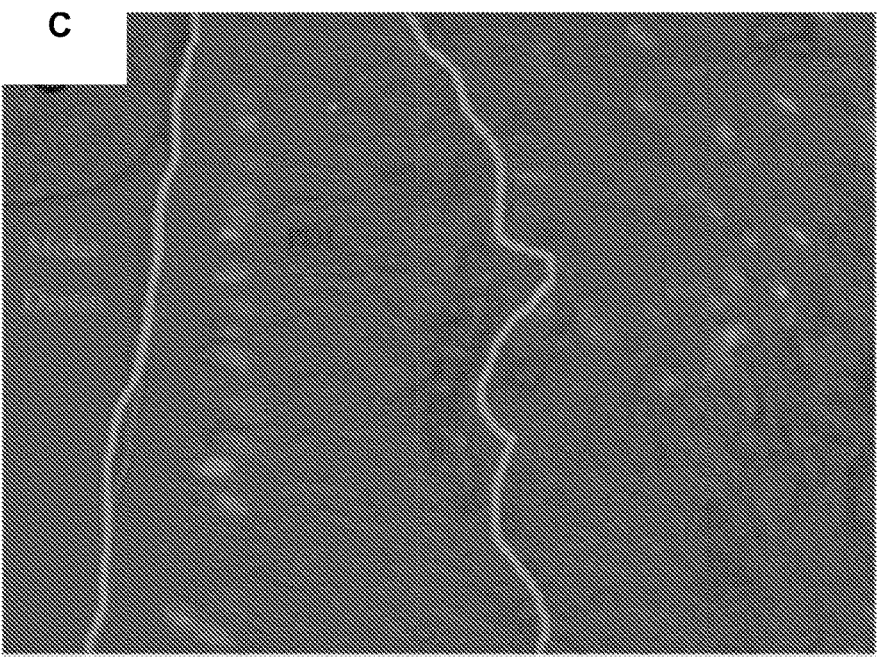

Col1a1 (2.3 kb)-Cre mouse was crossed with Rosa26R mouse and the GFP positive cells are osteoblast lineage cells. The results show that PDL cells connecting to the tooth are osteoblast lineage cells (see e.g., FIG. 5A-C).

Example 4

This example shows the expression and purification of the recombinant protein, amelogenin, and confirmation of the His-tagged amelogenin.

Figures 6A, 6B:
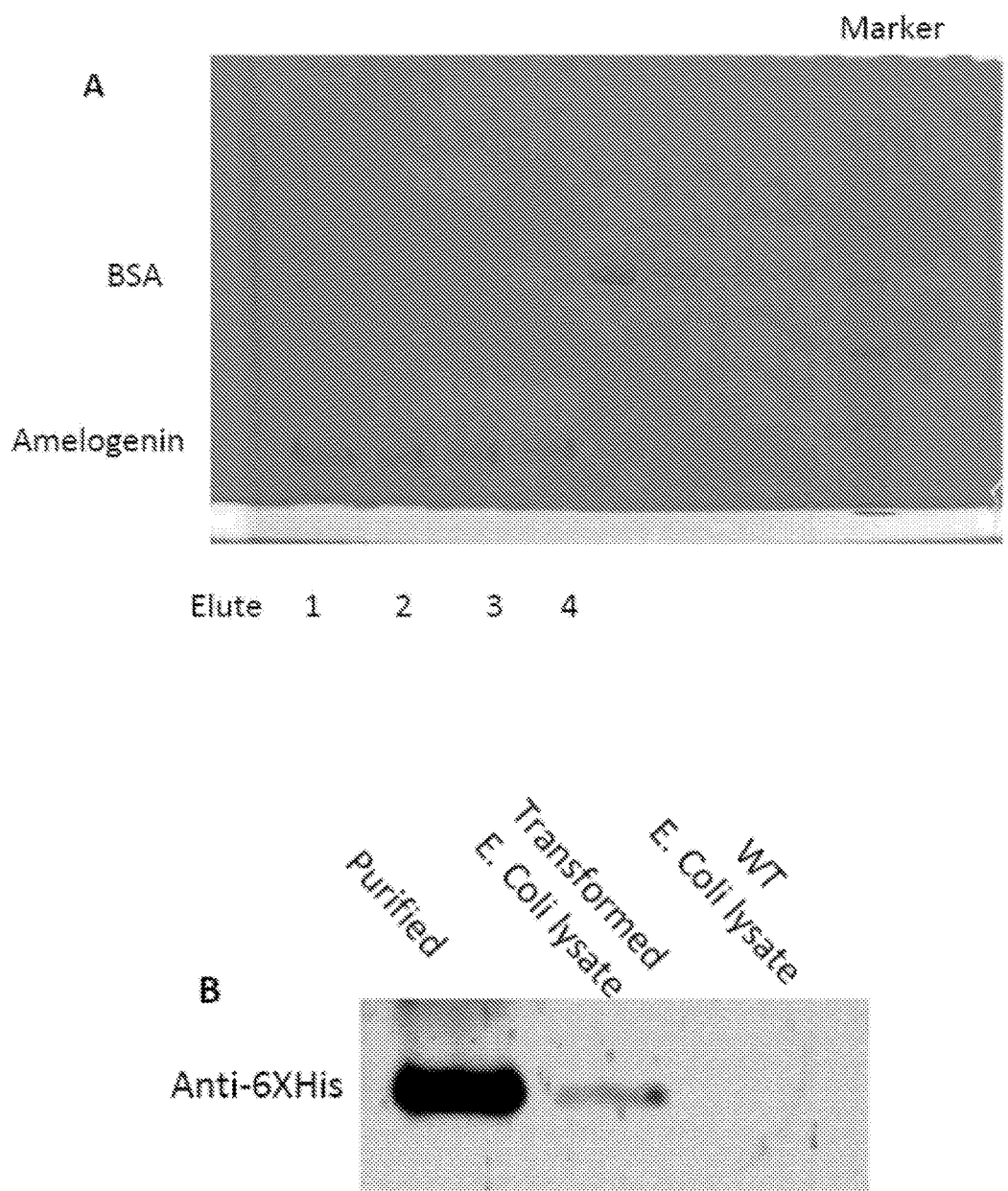
FIG. 6A-6B is a SDS-PAGE gel to examine the purity of the amelogenin protein.

The recombinant mouse amelogenin (rM179) was cloned into expression vector, pDEST17 and verified by sequencing using M13 primers. For expression in *Escherichia coli* (*E. coli*), pDEST17-amelogenin containing the T7 promoter was transformed into a BL21(DE3)pLysS (Invitrogen) strain. Selected colonies were grown in Luria-Bertani medium at 37° C. until the optical density of the culture reached 0.4-0.5 when measured at 600 nm. 0.7 mM isopropylthio-b-D-galactoside (IPTG) was added to induce the expression of recombinant amelogenin. The cells were harvested and resuspended in a bacterial protein extraction reagent (B-per, Pierece) containing 8 M Guanidine Chloride and sonicated until the *E coli* were lysed completely. The lysed cells were centrifuged for 15 min at 12,000 g. The supernatants were incubated with Hispure Cobalt resin at room temperature for 1 hour. The resin was then washed with PBS containing 1% triton and 8M Guanidine Chloride for 3 times. Then the protein was eluted with 0.5M EDTA containing 8M Guanidine Chloride. The eluted protein was then dialyzed with PBS containing 4M, 2M, 1M, 0.5M, 0.1M and 0M urea sequentially. The protein were then loaded on 10% SDS-PAGE gel to examine the purity (see e.g., FIG. 6A). The His tagged amelogenin was confirmed by western blotting using anti-His antibody (see e.g., FIG. 6B).

Example 5

This example shows the Isolation and Amolegenin-mediated Odontogenesis and Osteogenesis of Dental Stem Cells.

Exfoliating deciduous incisors and permanent third molars of multiple donors were collected. Dental pulp (DP) and periodontal ligament (PDL) stem cells were isolated and enzyme-digested per known methods (Yang et al., 2010, Clones of ectopic stem cells in the regeneration of muscle defects in vivo. PloS One. 2010 Oct. 20; 5 (10)). Mononucleated and adherent cells were cultured in DMEM-LG medium containing 10% FBS and 1% antibiotics in 10 cm cell culture dishes. These isolated cells contain single clones of multipotent stem cells that readily express stemness markers such as Stro-1, Oct4, Nanog, and CD146. DSCs and PDL cells were expanded and subjected to osteogenic and odontogenic differentiation. Briefly, DP and PDL stem cells were cultured in DMEM-LG medium containing 10% FBS, 50 µg/ml ascorbic acid and 1 mM 2-glycerophosphate in the presence or absence of recombinant amelogenin. The osteoaenic and odontoaenic differentiation was determined by the expression of RUNX2, dentin sialophosphoprotein (DSPP) and Dentin Matrix Protein 1 (DMP-1) by Real Time PCR, as well as Von Kossa and alkaline phosphatase staining. The level of active P-catenin was measured by immunefluorescence staining and western blotting.

Example 6

This example shows beta-catenin levels and staining in PDL cells treated with amelogenin. Amelogenin enhances osteogenesis and odontogenesis via beta-catenin pathway.

Figures 7A, 7B, 7C, 7D, 7E, 7F:
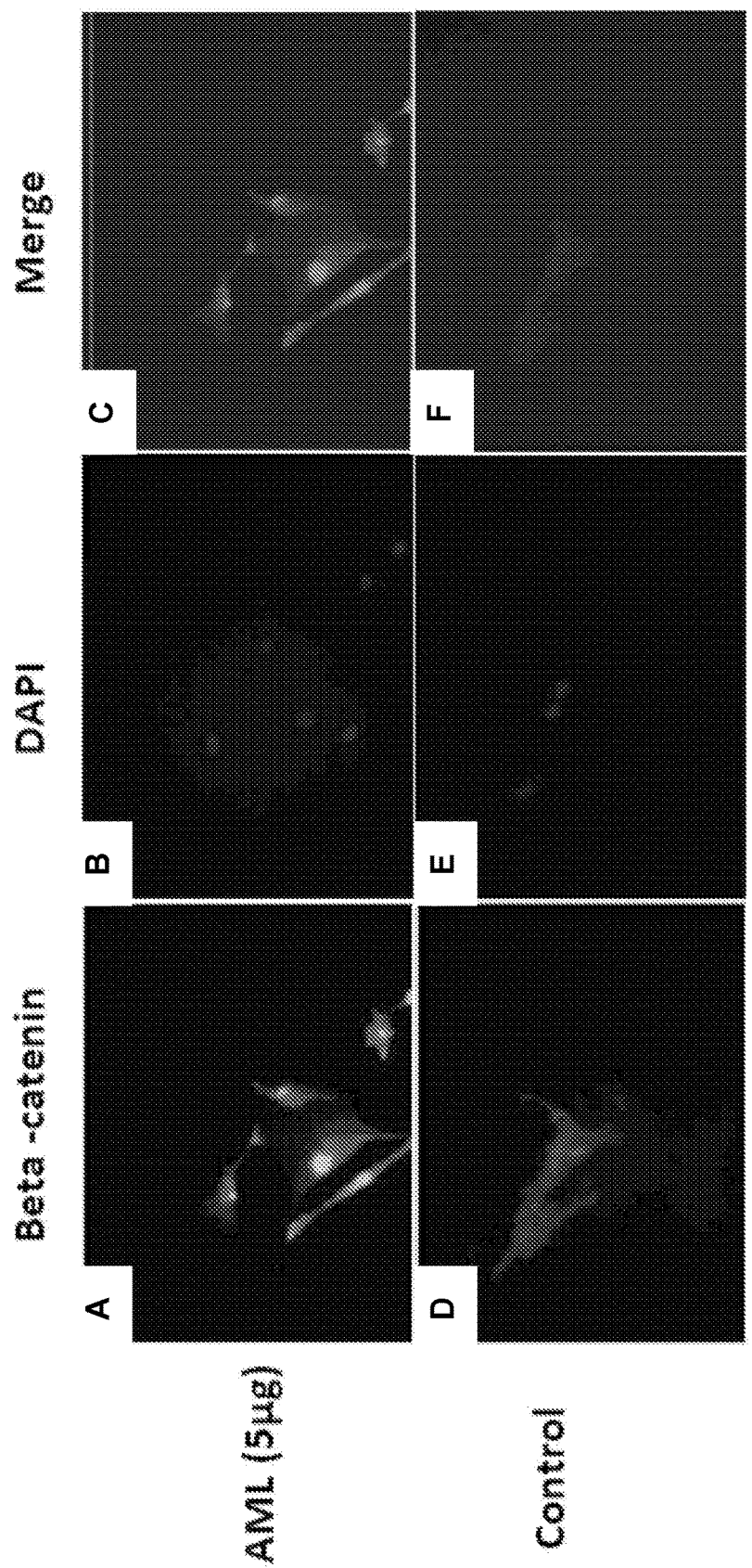
Figure 7G:
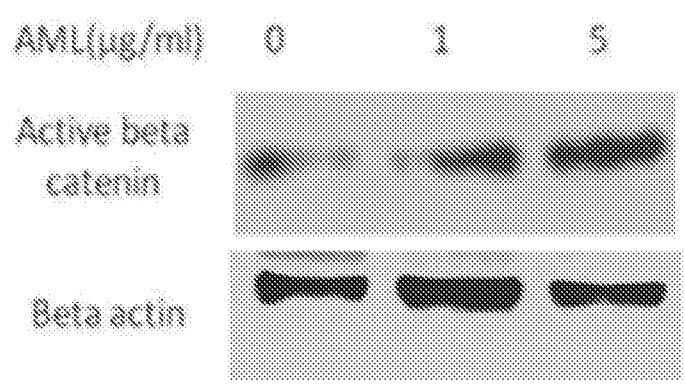

The PDL cells were treated with recombinant amelogenin overnight. The translocation of beta catenin was determined by immunofluorescence staining (see e.g., FIG. 7A-F). Briefly, the cells were fixed with formalin for 5 min and treated with PBS with 0.1% triton for 5 min. The cells were then incubated with anti-beta catenin antibody overnight, after washing with PBS with 0.5% Tween-20, then incubated with secondary antibody labeled with fluorescence dye. With the treatment of amelogenin, beta catenin translocalized into nucleus. Meanwhile, the PDL cells treated with amelogenin were lysed with PBS lysis buffer containing 1% NP-40 and protease inhibitor, phisphotase inhibitor cocktails. The non-phosphorylated beta catenin levels were determined by western blotting using anti-active beta catenin antibody (anti-ABC, millipore) (see e.g., FIG. 7G).

Example 7

This example shows amelogenin-induced beta-catenin signaling levels in dental pulp cells and increased non-phosphorylated beta-catenin levels.

Figure 8G:
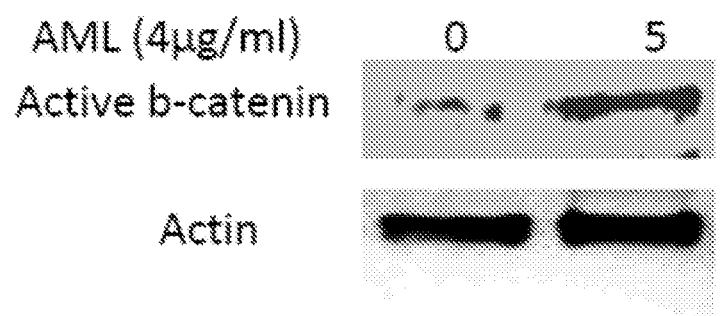

The dental pulp cells were treated with recombinant amelogenin overnight. The translocation of beta catenin was determined by immunofluorescence staining (see e.g., FIG. 8A-F). Briefly, the cells were fixed with formalin for 5 min and treated with PBS with 0.1% triton for 5 min. The cells were then incubated with anti-beta catenin antibody overnight, after washing with PBS with 0.5% Tween-20, then incubated with secondary antibody labeled with fluorescence dye. With the treatment of amelogenin, beta catenin translocalized into nucleus. The PDL cells treated with amelogenin were lysed with PBS lysis buffer containing 1% NP-40 and protease inhibitor, phosphatase inhibitor cocktails. The non-phosphorylated beta-catenin levels were determined by western blotting using anti-active beta catenin antibody (anti-ABC, millipore) (see e.g., FIG. 8G).

Example 8

This example shows that in PDL cells treated with amelogenin exhibited active beta-catenin levels, nuclear translocalization, and increased Wnt and LacZ activity. Upregulated beta-catenin leads to the expression of genes that facilitate osteogenic and odontogenic lineage differentiations. Given co-localization with canonical Wnt signaling, amelogenin enhances odontogenesis and osteogenesis by modulating the Wnt/beta-catenin signaling pathway.

Figures 18A, 18B, 18C, 18D, 18E, 18F:
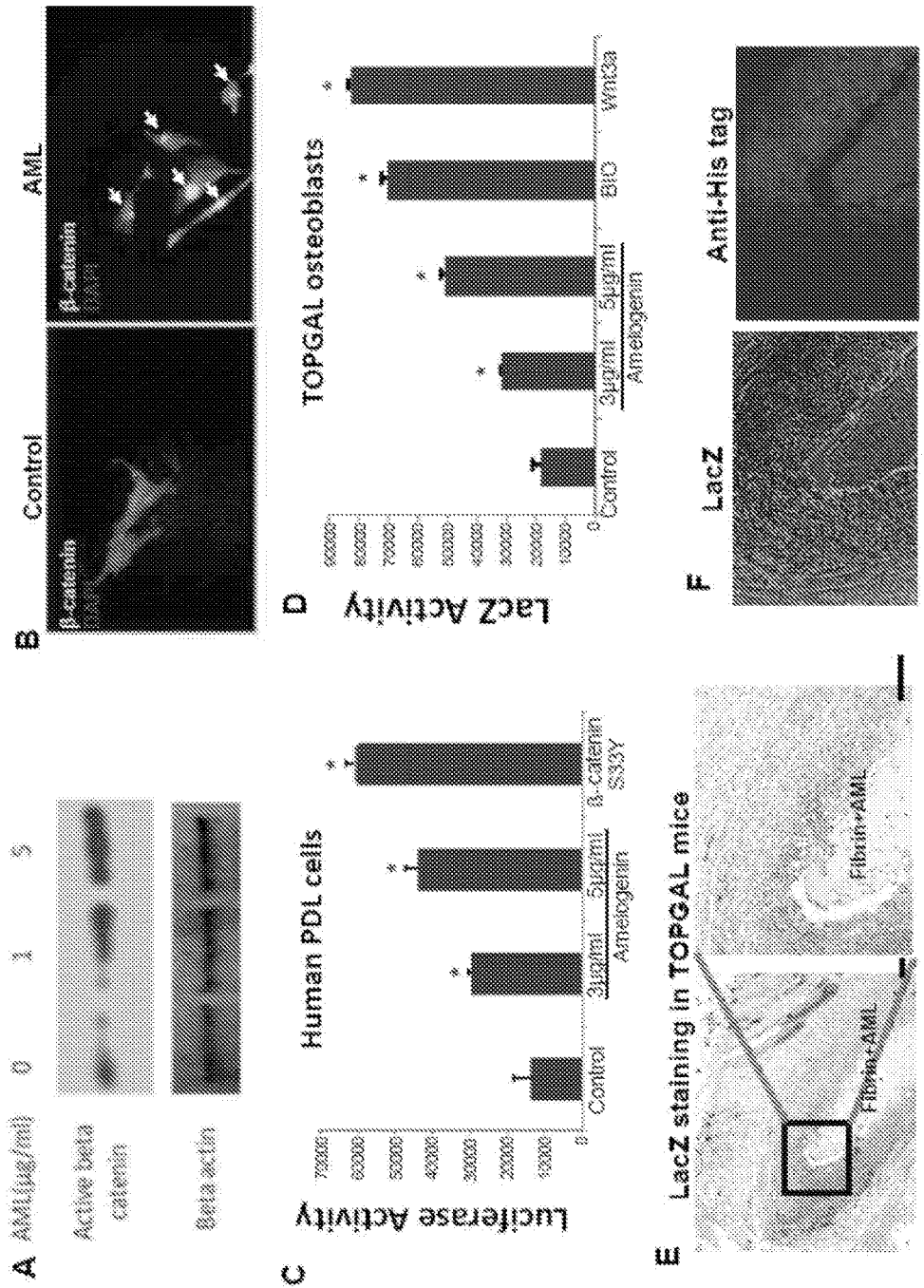
FIG. 18A-18F is a western blot of active beta catenin.

PDL cells were treated with amelogenin for 16 hours. The active beta catenin level were determined by western blotting (see e.g., FIG. 18A). The nuclear translocalization was demonstrated by immunofluorescence staining (see e.g., FIG. 18B). Wnt signaling reporter TOPFLASH was transfected into PDL cells and then the cells were treated with amelogenin. The luciferase activity was measured 48 hours after treatment (see e.g., FIG. 18C). The primary osteoblasts were isolated from Wnt signaling reporter mice, TOPGAL. 48 hours after treatment, the LacZ activity was measured (see e.g., FIG. 18D). Fibrin gel containing 50 µg/ml was implanted subcutaneously into the TOPGAL mice. 1 week post-implantation, the gel was harvested. LacZ staining was performed. The LacZ positive cells were found in the surrounding area of the gel where beta catenin signaling activation was found (see e.g., FIG. 18E). Recombinant amelogenin is 6×His tagged. The distribution of amelogenin is shown overlapped with the beta catenin signaling as indicated by the LacZ staining (see e.g., FIG. 18F).

Example 9

This example shows a temporal increase in cell counts in PDL cells treated with amelogenin.

Figure 9A:
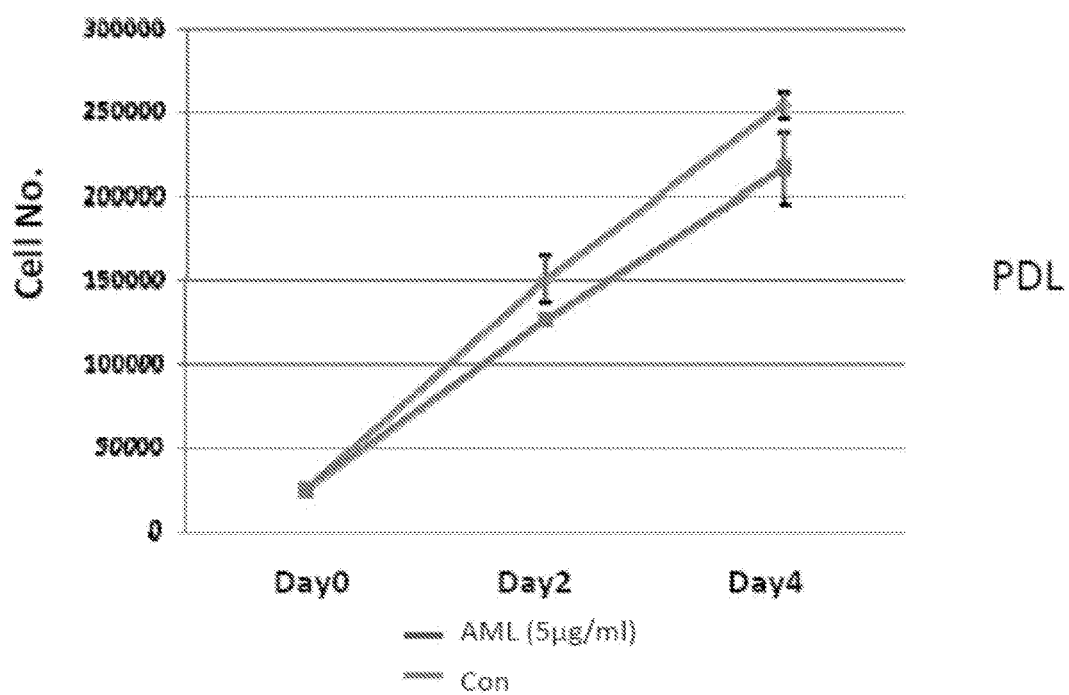
FIG. 9A-9B is a pair of graphs showing cell no. (or count) vs. Day 0, 2, and 4 post-treatment of AML.
Figure 9B:
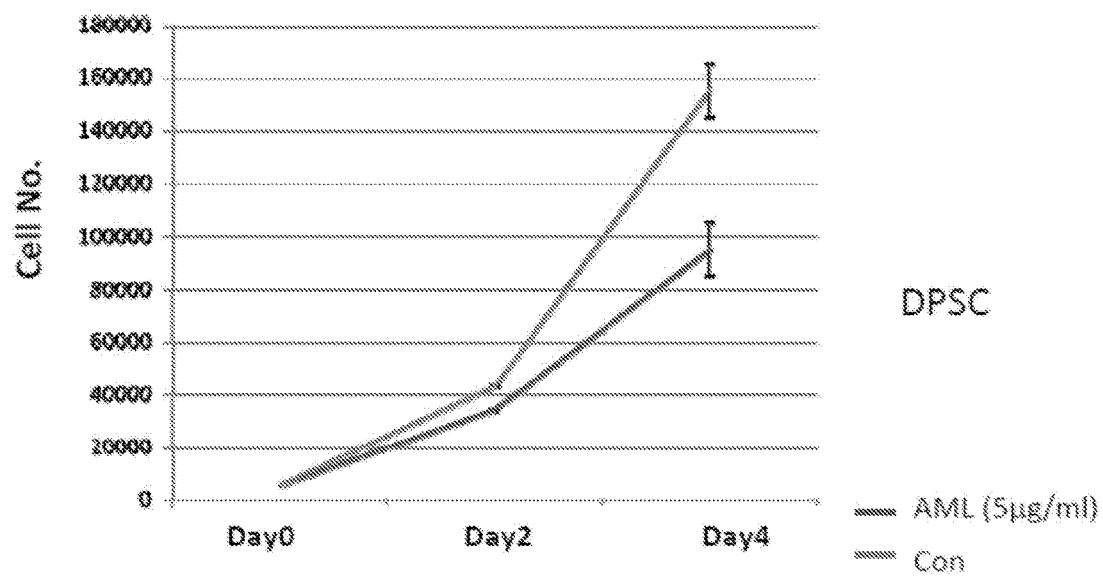

PDL cells and dental pulp cells (DPSC) were seeded in 12 well plate with the cells number indicated. The cell treated with amelogenin and cell number were counted at 0, 2, and 4 days (see e.g., FIG. 9A-B).

Example 10

This example shows osteogenic differentiation in PDL cells cultured in osteogenic medium.

Figure 10:
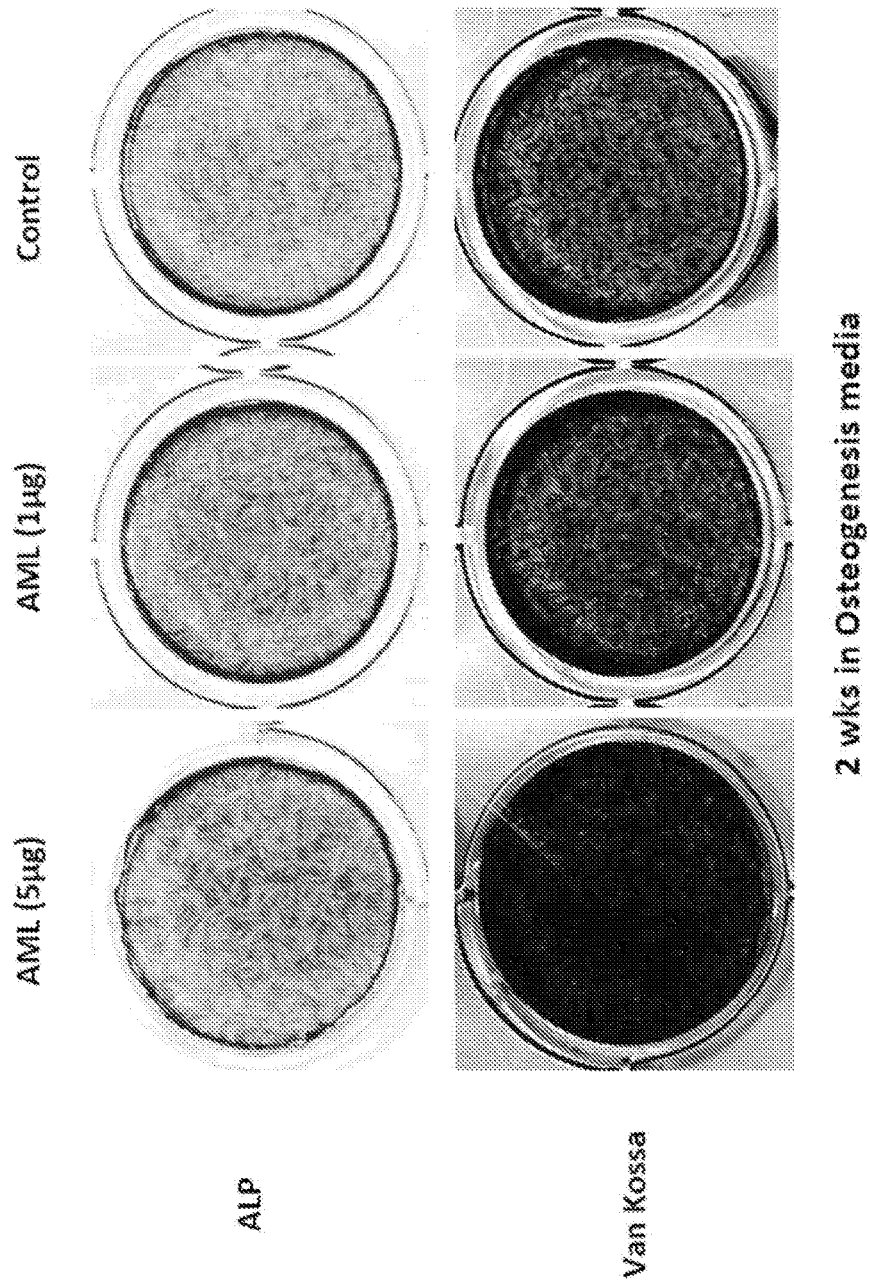
FIG. 10 are a series of images of PDL cells cultured in osteogenic medium for two weeks, then stained with Alkaline phosphotase (ALP) and Van Kossa to observe osteogenic differentiation.

PDL cells were cultured in osteogenic medium containing 10 mM beta glycerophosphate, 50 µg/ml Ascorbic acid, and 1 mM Dexamethasone for 2 weeks, the cells were then stained with Alkaline phosphotase and Van Kossa staining to demonstrate the osteogenic differentiation (see e.g., FIG. 10).

Example 11

This example shows marker gene RunX2 and DSPP expression in PDL cells cultured in osteogenic medium.

Figures 11A, 11B, 11C:
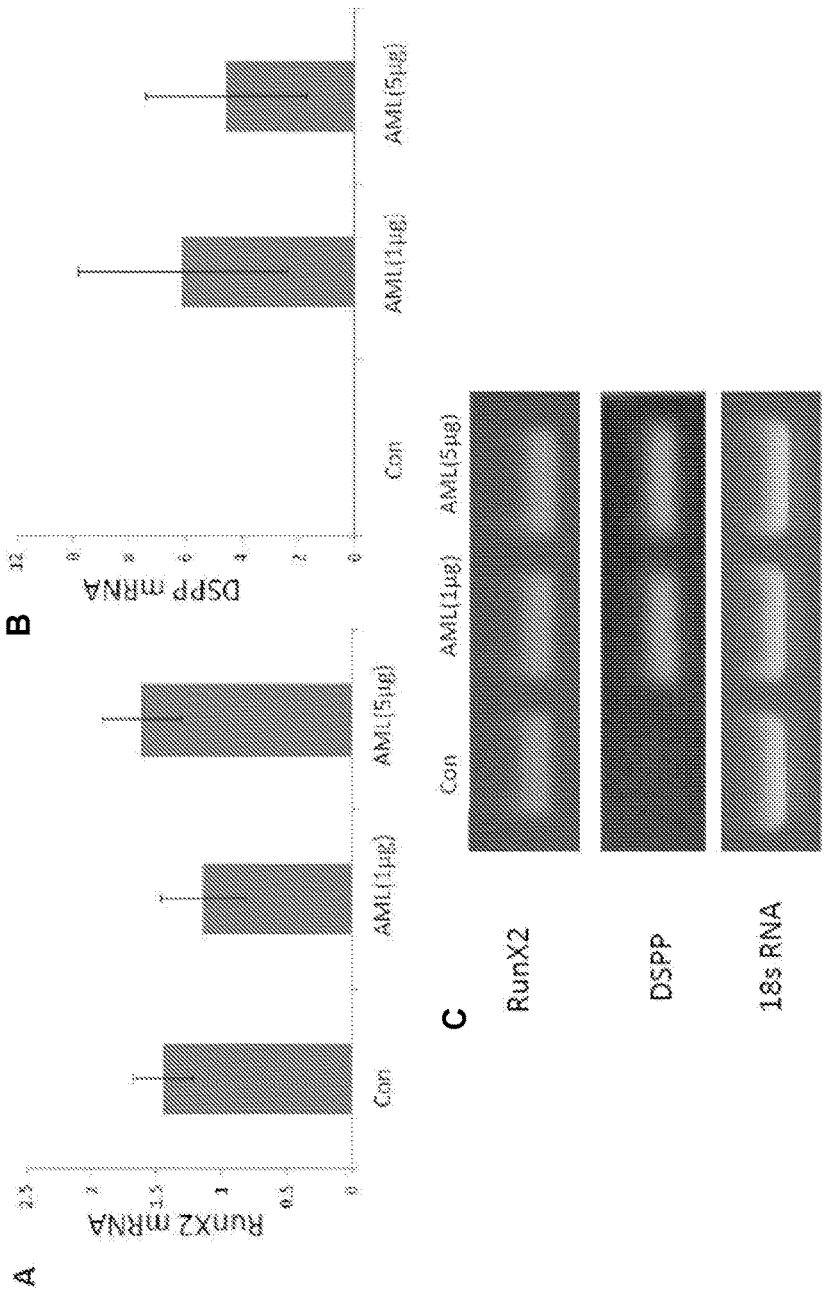
FIG. 11A-11C is a pair of bar graphs, RT-PCR, and gel electrophoresis data.
Figures 12A, 12B, 12C, 12D, 12E:
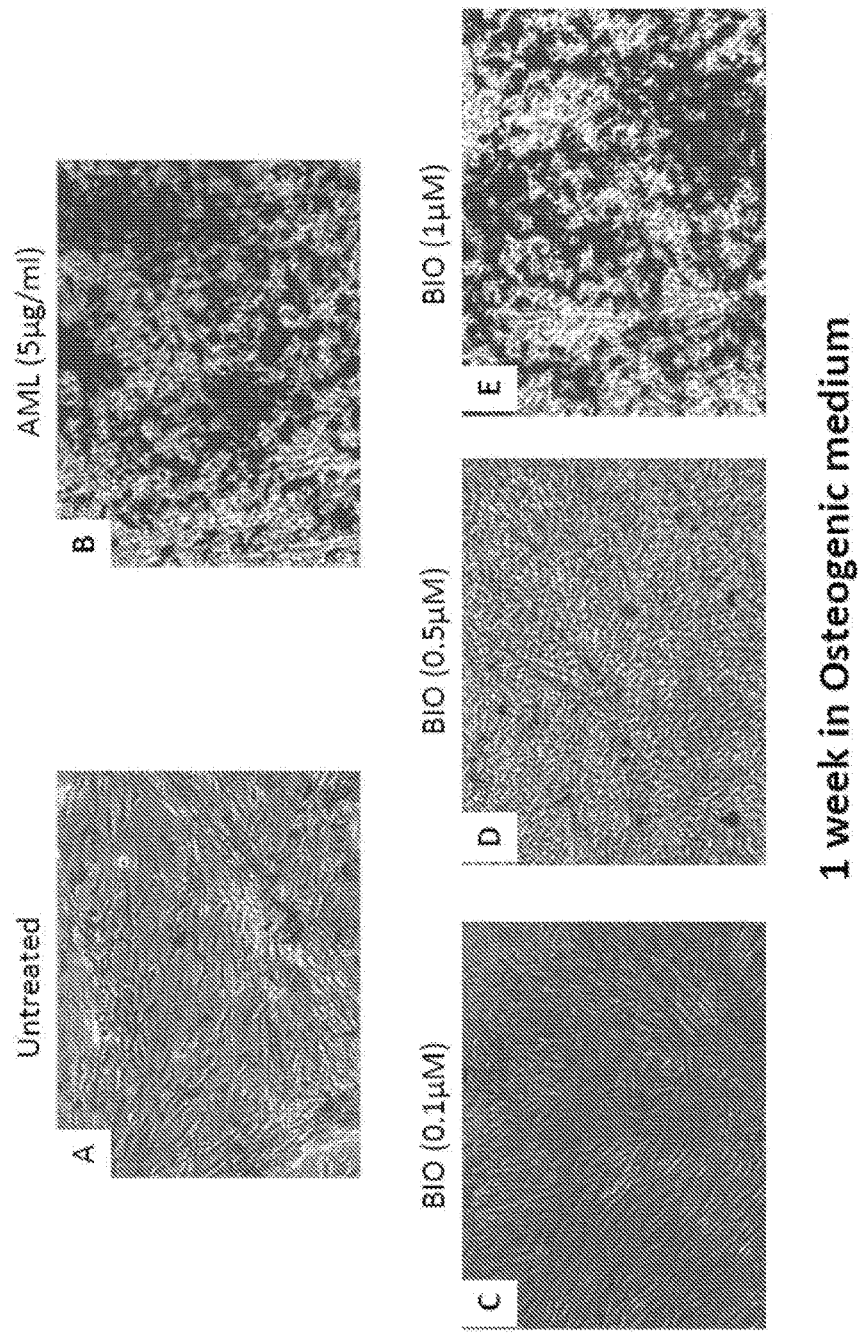
FIG. 12A-12E is a series of light microscopy images of PDL cells untreated (FIG. 12A), 5 μg/ml AML-treated (FIG. 12B), 0.1 μg/ml BIO-treated (FIG. 12C), 0.5 μg/ml BIO-treated (FIG. 12D), and 1 μg/ml BIO-treated PDL cells (FIG. 12E), respectively after one week in osteogenic medium.

RNA was extracted from PDL cells cultured in osteogenic medium for 2 weeks. The expression marker genes, RunX2 and DSPP, were determined by Real Time PCR (see e.g., FIGS. 11A-B) and confirmed by gel electrophoresis (2% agarose gel) (see e.g., FIG. 11C).

Example 12

This examples show that PDL cells treated with amelogenin and Wnt in osteogenic medium displayed similar calcified matrix staining.

PDL cells were treated with amelogenin (AML) and Wnt signaling agonist (BIO) in osteogenic medium for a week (see e.g., FIGS. 12A-E). The Amelogenin-treated cells (see e.g., FIG. 12B) and the 1 µM BIO-treated (see e.g., FIG. 12E) cells displayed a similar amount of calcified matrix staining (Van Kossa) after one week in osteogenic medium.

Example 13

This example shows osteogenic differentiation and expression of marker genes, RunX2 and DSPP in dental pulp stem cells cultured in osteogenic medium in the AML-treated group.

Figures 13A, 13B, 13C, 13D:
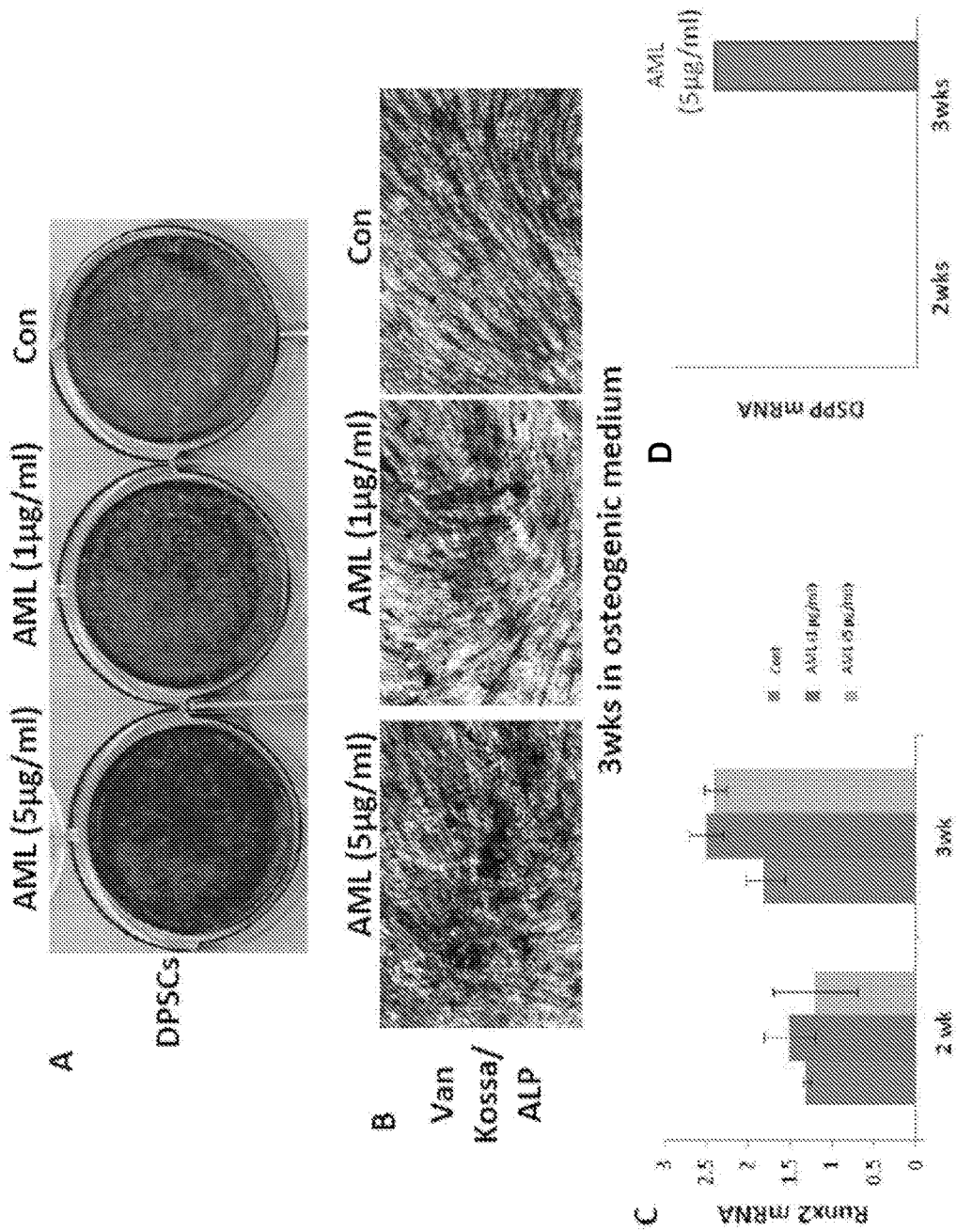
FIG. 13A-13D is a series of images and bar graphs of dental pulp stem cells cultured in osteogenic medium.

Dental pulp stem cells (DPSCs) were cultured in osteogenic medium for 3 weeks (see e.g., FIG. 13A-B). The osteogenic differentiation was determined by ALP and Van Kossa staining (see e.g., FIG. 13B). The expression of marker genes, RunX2 and DSPP, were determined by RT-PCR (see e.g., FIG. 13C). The amelogenin-treated group showed DSPP-positive results (see e.g., FIG. 13D).

Example 14

This example shows cell differentiation in C3H10t1/2 cells cultured in osteogenic medium at two weeks.

Figures 14A, 14B, 14C:
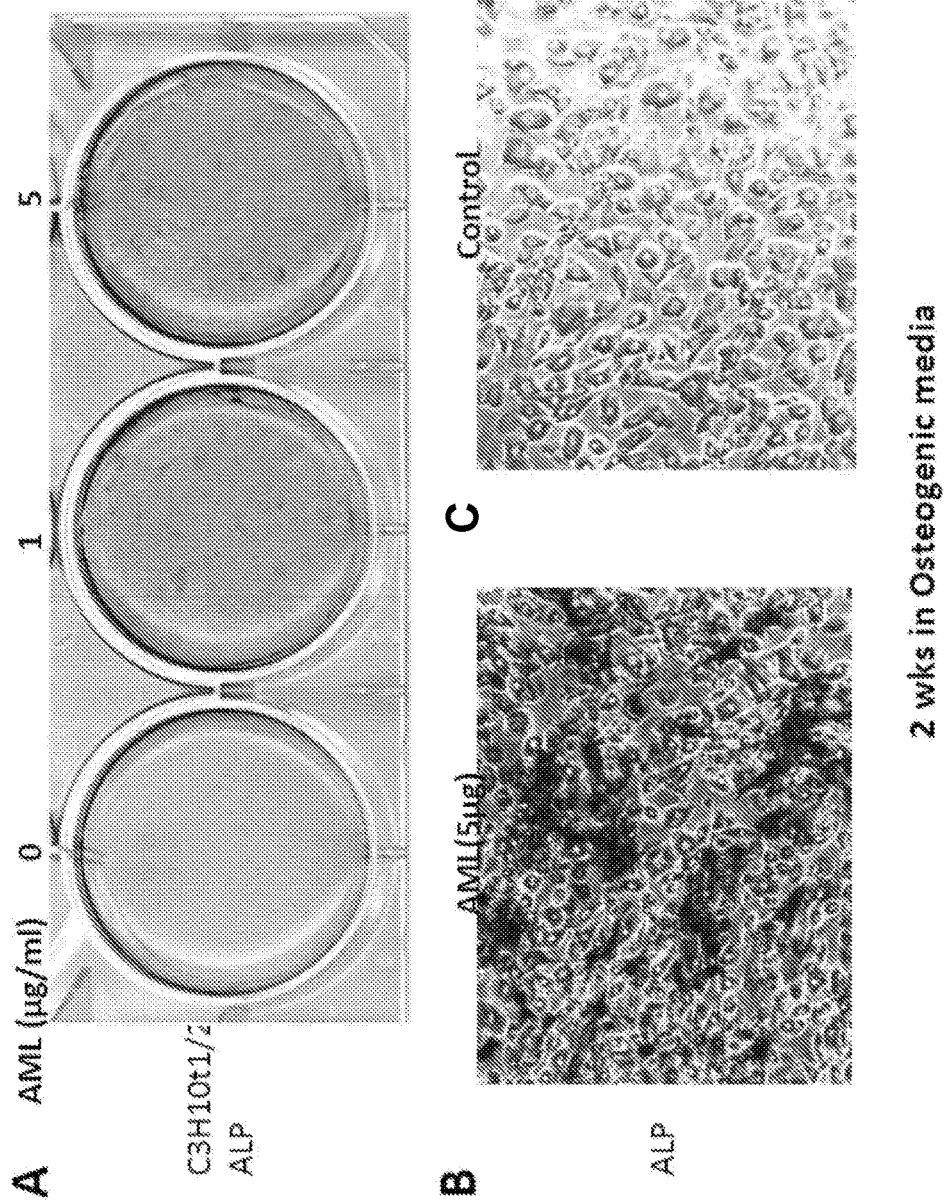
FIG. 14A-14C are images of C3H10t1/2 Mesenchymal stem cells cultured in osteogenic medium at two weeks.

Mesenchymal stem cell C3H10t1/2 cells were cultured in osteogenic medium for 2 weeks (see e.g., FIG. 14A). The cell differentiation was determined by ALP staining and Van Kossa staining when compared to the control (see e.g., FIG. 14B-C). Only cells treated with amelogenin showed positive for ALP, but negative for Van Kossa staining.

Example 15

This example shows that amelogenin-treated cells were positive for ALP and Van Kossa staining and expressed RunX2 at three weeks.

Figures 15A, 15B, 15C:
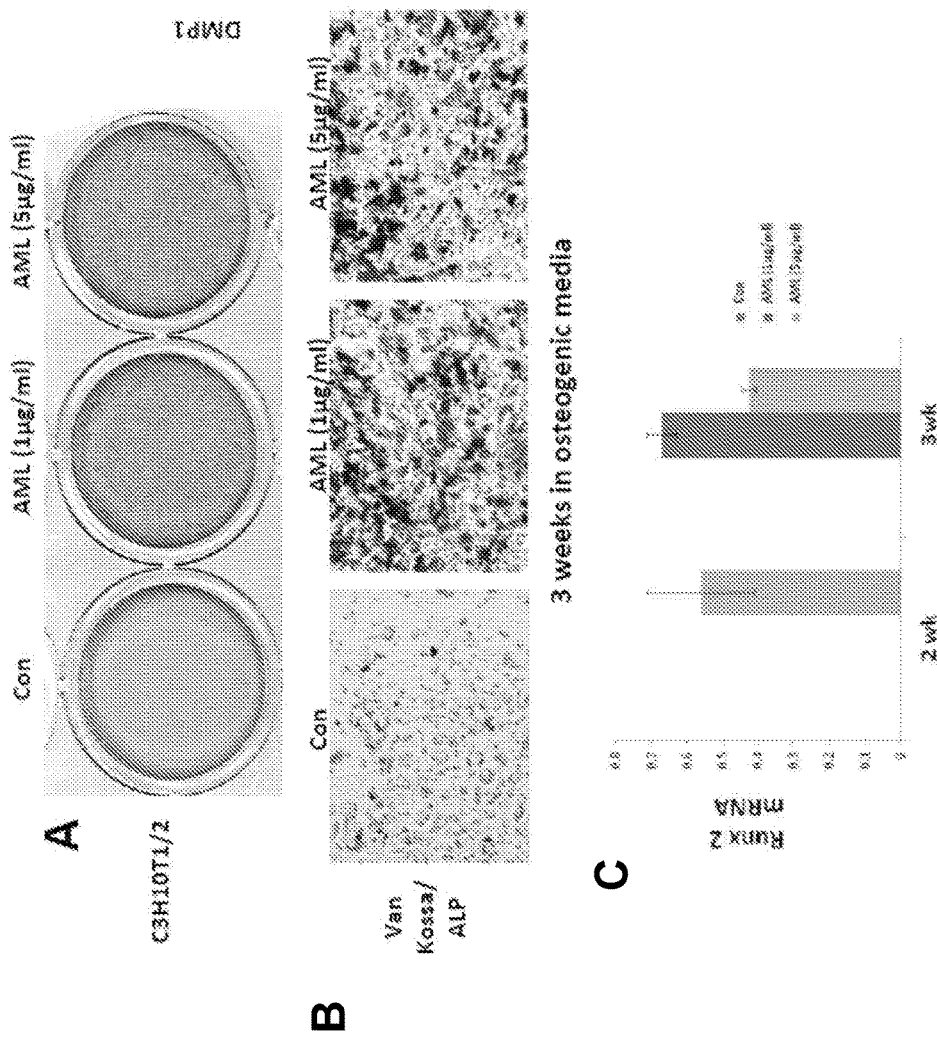
FIG. 15A-15C are images of C3H10t1/2 Mesenchymal stem cells cultured in osteogenic medium at three weeks.

At 3 weeks, amelogenin-treated cells were positive for both ALP and Van Kossa (see e.g., FIG. 15A-B). RT-PCR demonstrated amelogenin induced RunX2 expression (see e.g., FIG. 15C). However, the cells tested negative for DSPP.

Example 16

This example shows in vitro cell migration of PDL cells was performed using the Boyden assay for different methods of amelogenin addition.

Figures 20A, 20B:
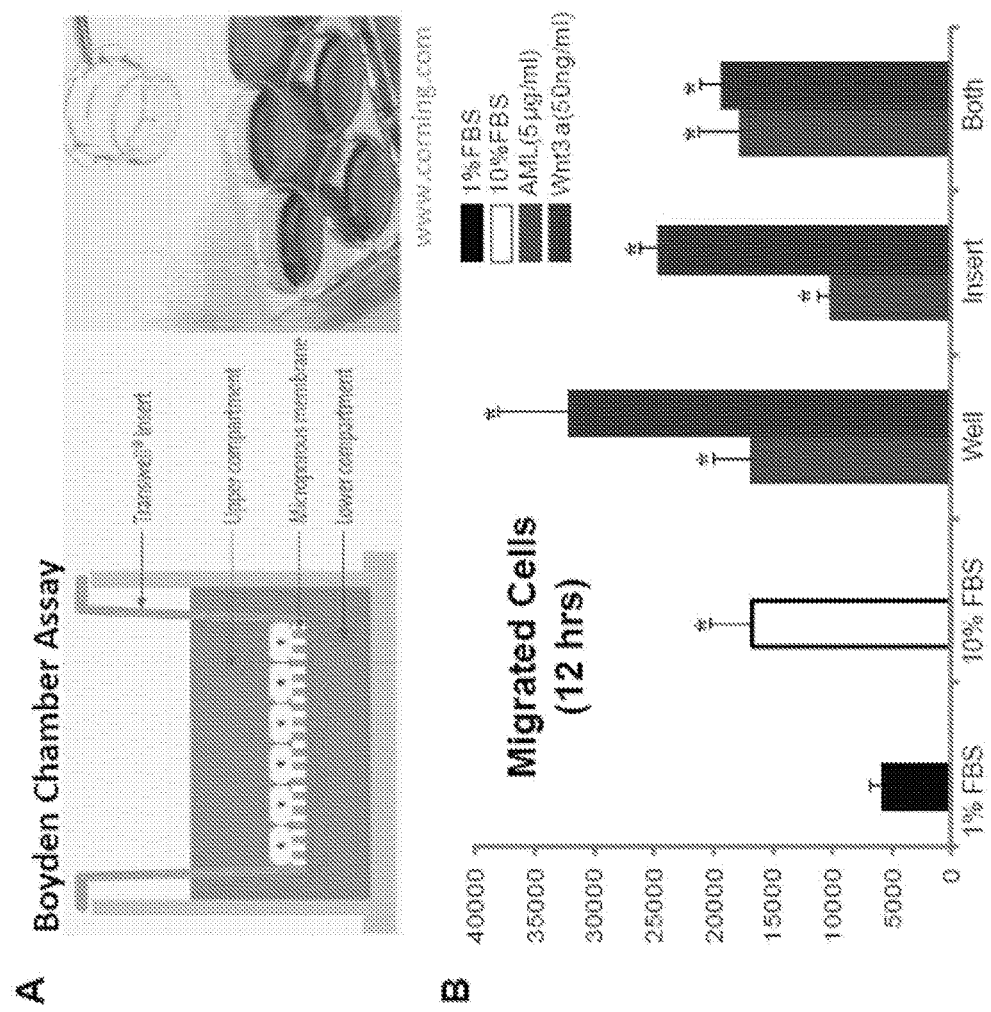
FIG. 20A is an illustration of the Boyden assay and FIG. 20B is a bar graph showing the cell count of cells that migrated after 12 hours (using the Boyden assay) to the chamber according to where the AML was inserted (i.e., well, insert, or both).

The PDL cell migration was determined by Boyden Chamber assay. 0.2 million cells were seeded in the insert and 1% serum, 10% serum DMEM media were added to the chamber. DMEM containing 5 µg/ml amelogenin was added to the chamber (well), insert or both (see e.g., FIG. 20A). 12 hours later, the migrated cells were counted (see e.g., FIG. 20B).

Figure 16:
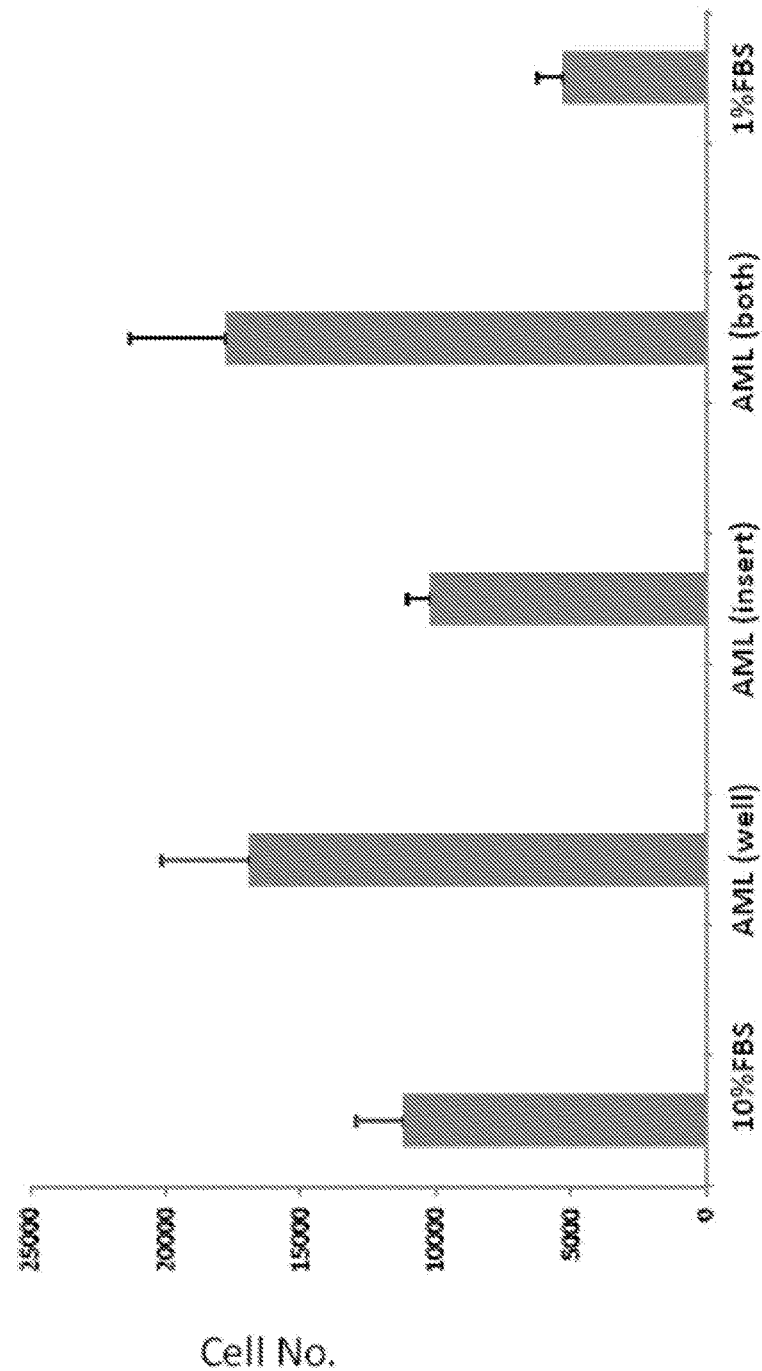
FIG. 16 is a bar graph showing the cell count of cells that migrated (using the Boyden assay) to the chamber according to where the AML was inserted (i.e., well, insert, or both).

The PDL cells were synchronized by serum starvation for overnight. The cells were then seeded at 100,000 per insert in medium containing 1% serum. Amelogenin (5 µg/ml) was added to insert or/and chamber. 12 hours later, the cells migrated into the chamber were counted (see e.g., FIG. 16).

Example 17

In this example it was shown that amelogenin promoted the PDL cells matrix synthesis and upregulated the type I collagen mRNA; promoted cell differentiation, confirmed by Alkaline phosphatase and von Kossa staining; and promoted the upregulation of differential cell markers.

Figures 17A, 17B, 17C, 17D, 17E, 17F, 17G:
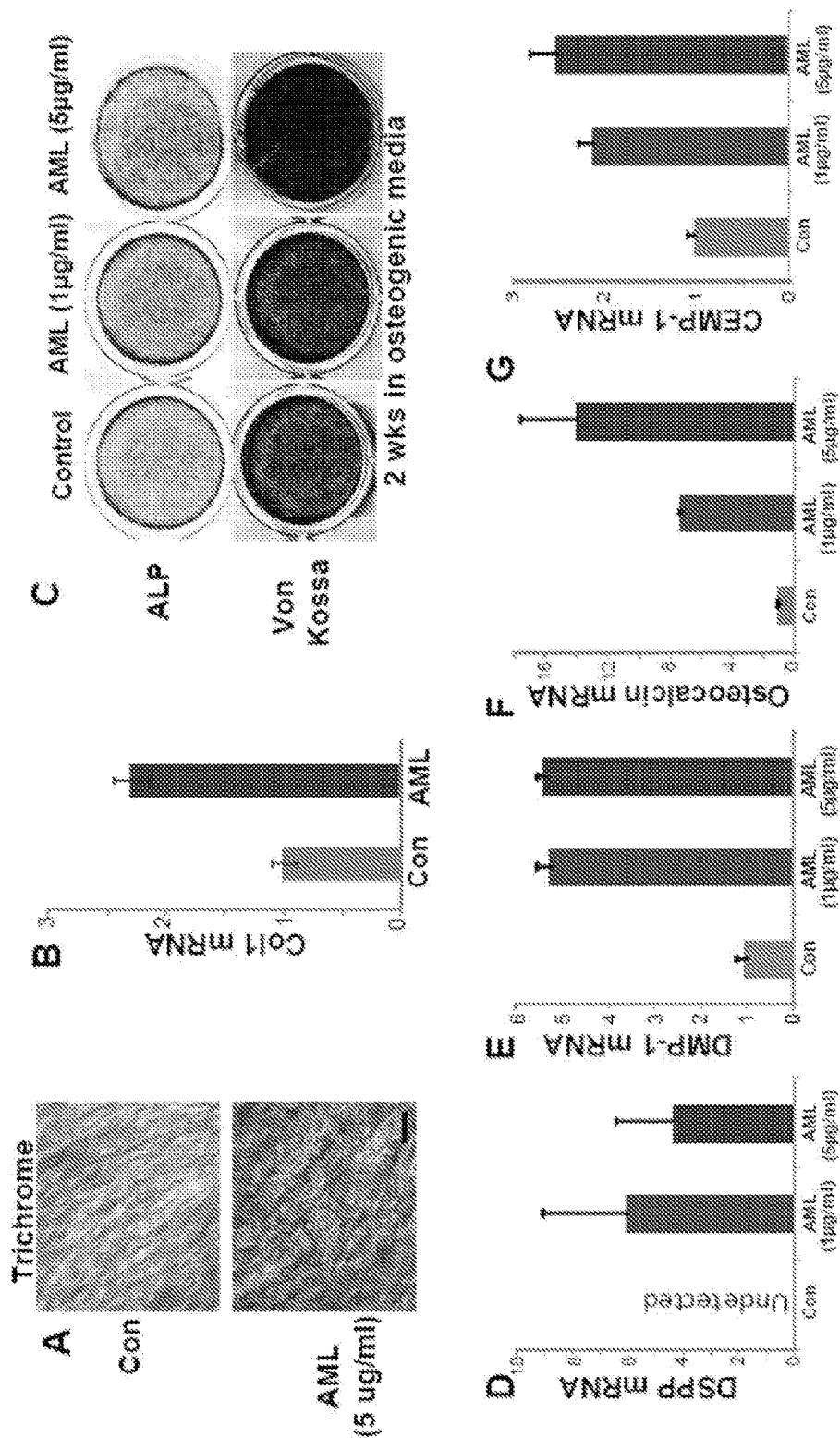
FIG. 17A-17G is a series of images and bar graphs describing the osteogenic differentiation and expression of differential cell markers in human PDL cells.

Human PDL cells were seeded in the 6 well plate and cultured in presence of 50 µg/ml ascorbic acid. The cells were treated with amelogenin. 2 weeks post-treatment, the cells were subjected to trichrome staining to demonstrate the expression of a collagen matrix (see e.g., FIG. 17A). Amelogenin was shown to promote the PDL cells matrix synthesis. The total RNA was extracted and the expression of type I collagen was determined by Real Time PCR (see e.g., FIG. 17B). Amelogenin was shown to upregulate the type I collagen mRNA. PDL cells were treated with amelogenin in the chemically-defined osteogenic media (see FIG. 17C). The cell differentiation was confirmed by Alkaline phosphatase and von Kossa staining. Real Time PCR showed the upregulation of differentiation markers (see e.g., FIG. 17D-G).

Example 18

This example shows that human PDL cells transfected with a Wnt signaling inhibitor, ICAT plasmid, then treated with amelogenin in osteogenic media demonstrated cell differentiation.

Figures 19A, 19B, 19C, 19D:
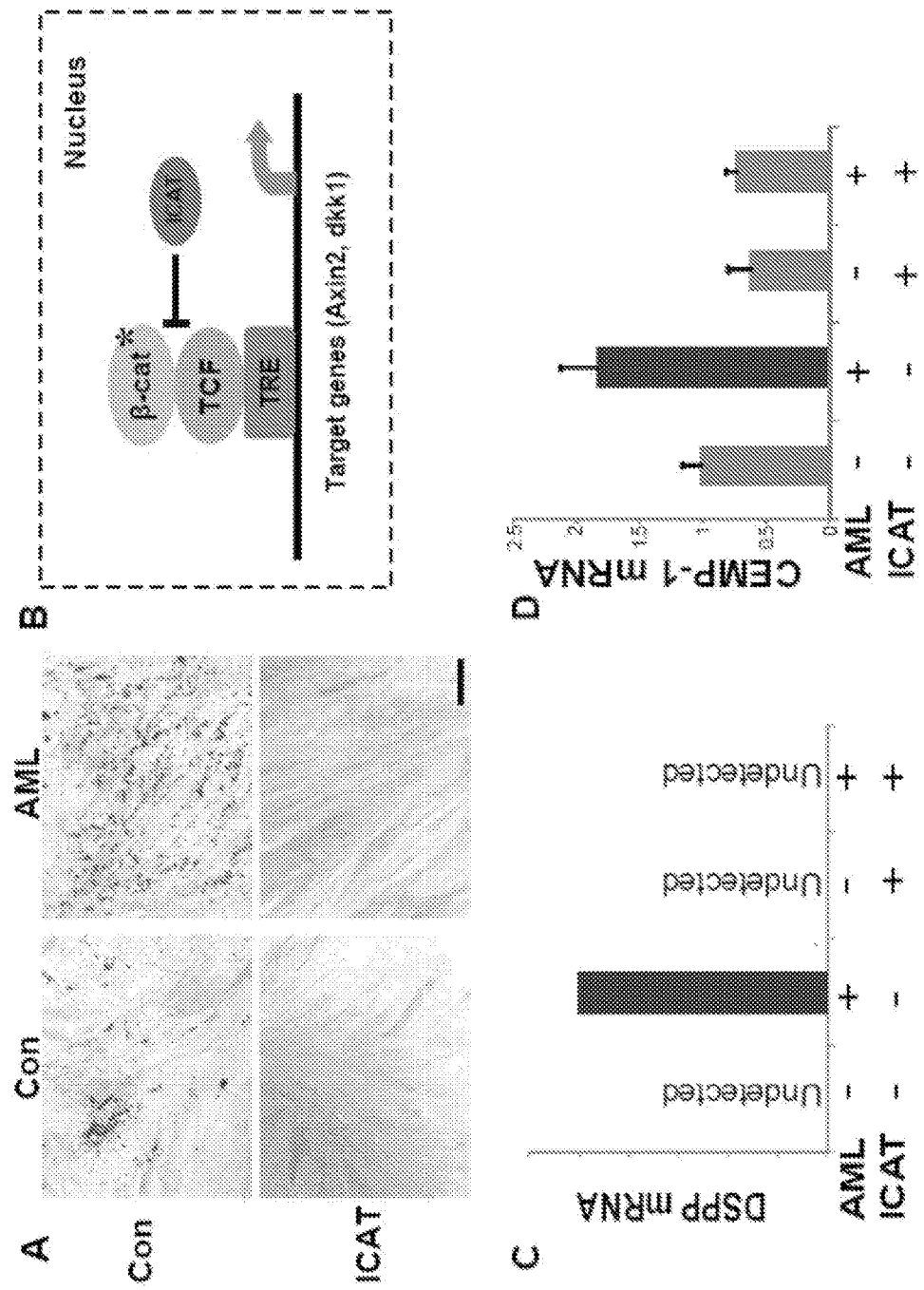
FIG. 19A-19D is a series of images, an illustration, and a pair of bar graphs demonstrating cell differentiation.

Human PDL cells were transfected with the Wnt signaling inhibitor, ICAT plasmid. The cells were treated with amelogenin in the osteogenic media for 2 weeks. Cell differentiation was demonstrated by Von Kossa staining (see e.g., FIG. 19A). The expression of differentiation markers were determined by Real Time PCR (see e.g., FIG. 19C-D).

Example 19

This example demonstrates cell differentiation and expression of differentiation markers in human PDL cells treated with amelogenin, BIO, or Wnt3A.

Figures 21A, 21B, 21C, 21D, 21E, 21F, 21G:
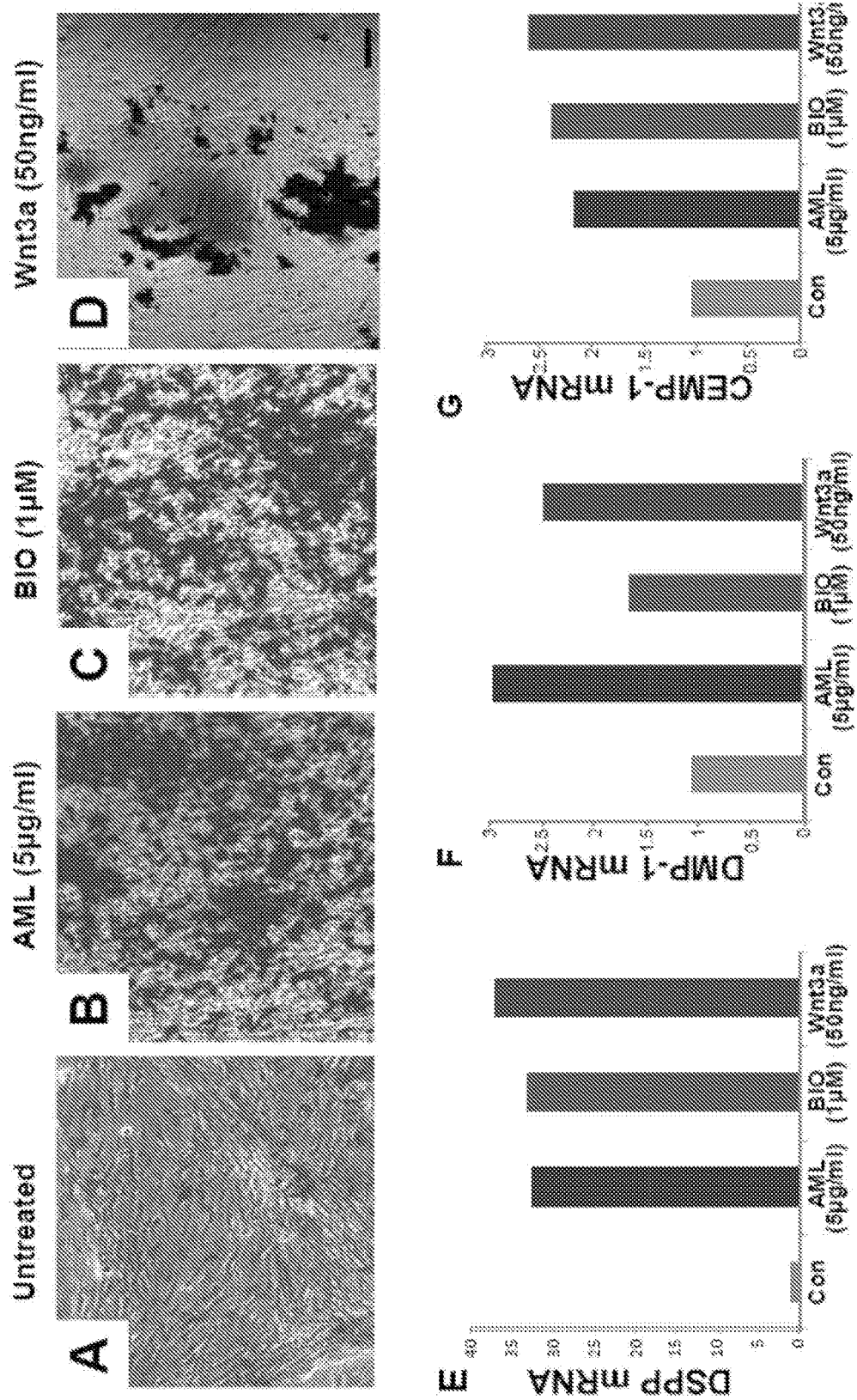
FIG. 21A-21G is a series of images and bar graphs illustrating the cell differentiation and expression of differentiation markers.

The human PDL cells were treated with amelogenin, BIO, or Wnt3A as indicated for 2 weeks. The cell differentiation was demonstrated by von Kossa staining (see e.g., FIG. 21A-D). PCR showed the expression of differentiation markers (see e.g., FIG. 21E-G).

Example 20

This example shows amelogenin expression and cell differentiation in human PDL cells transfected with PCMV6—amelogenin plasmid.

Figures 22A, 22B, 22C:
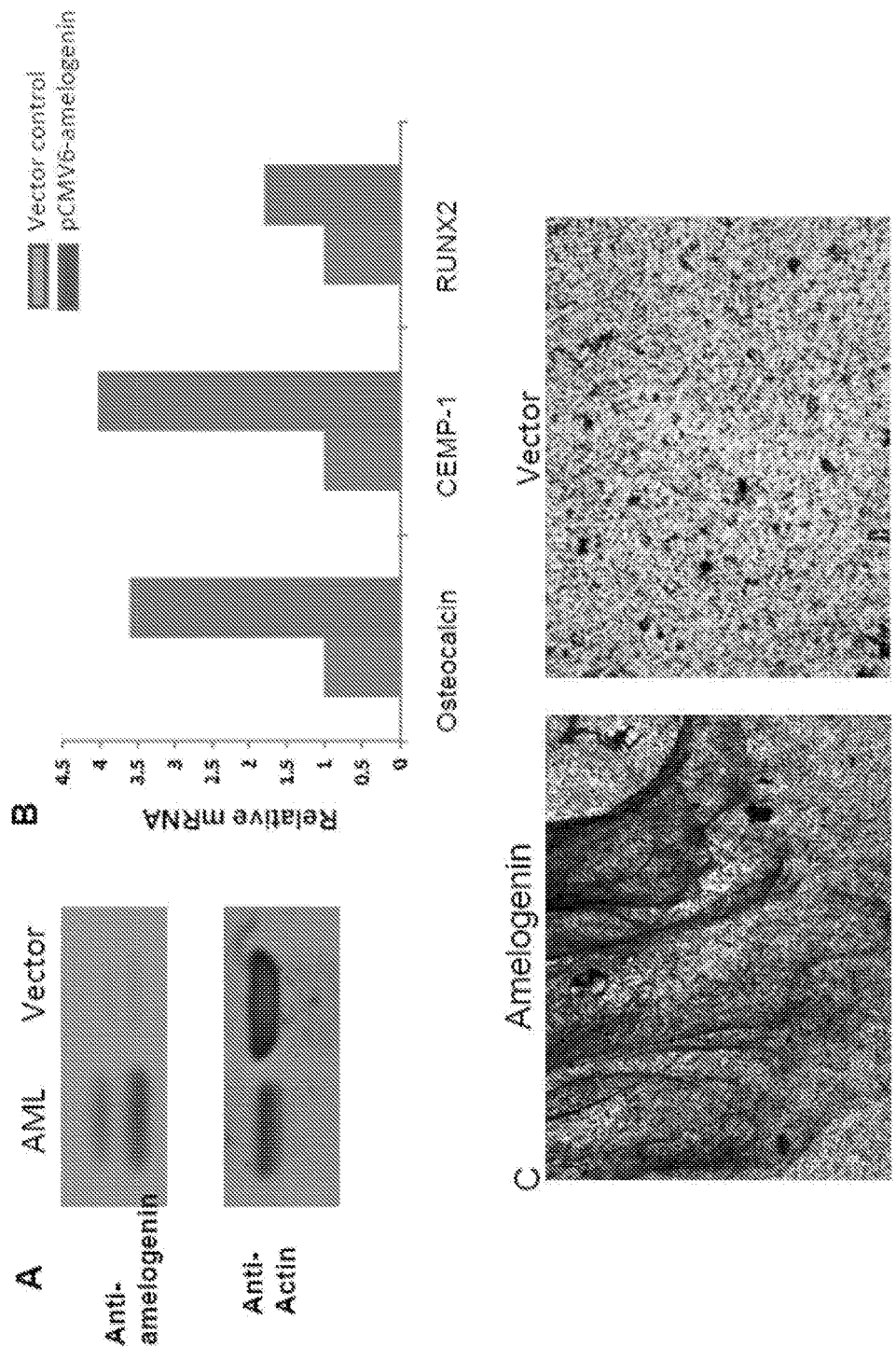
FIG. 22A-22C shows amelogenin expression and cell differentiation in human PDL cells transfected with PCMV6—amelogenin plasmid.

Human PDL cells were transfected with PCMV6—amelogenin plasmid or empty vector. The cells were then selected using 300 mg/ml G418. 2 weeks after selection, the cells formed colonies. The expression of amelogenin was confirmed by western blot (see e.g., FIG. 22A). The cells were then cultured in osteogenic media for 2 weeks and then cell differentiation was determined by marker gene expression (see e.g., FIG. 22B) and van Kossa staining (see e.g., FIG. 22C).

Example 21

This example demonstrates that cementum-like structures were formed in PDL cells stabilized with an amelogenin vector.

Figures 23A, 23B, 23C:
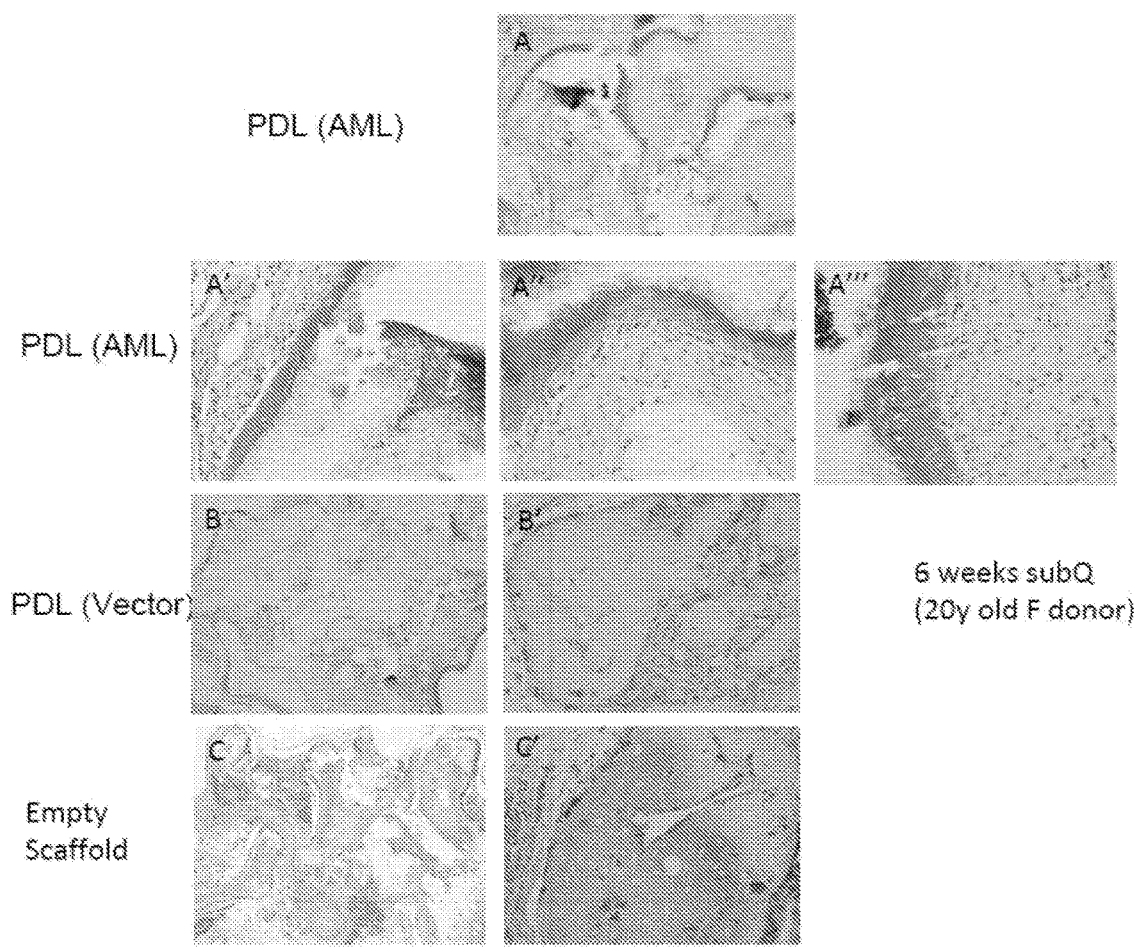
FIG. 23A-A''' is a series of images of H&E-stained sections of human PDL cells stabilized in an AML vector.
FIG. 23B-B' are images of H&E-stained sections of PDL cells in a control vector.
FIG. 23C-C' are images of H&E-stained sections of an empty scaffold.
Figure 24:
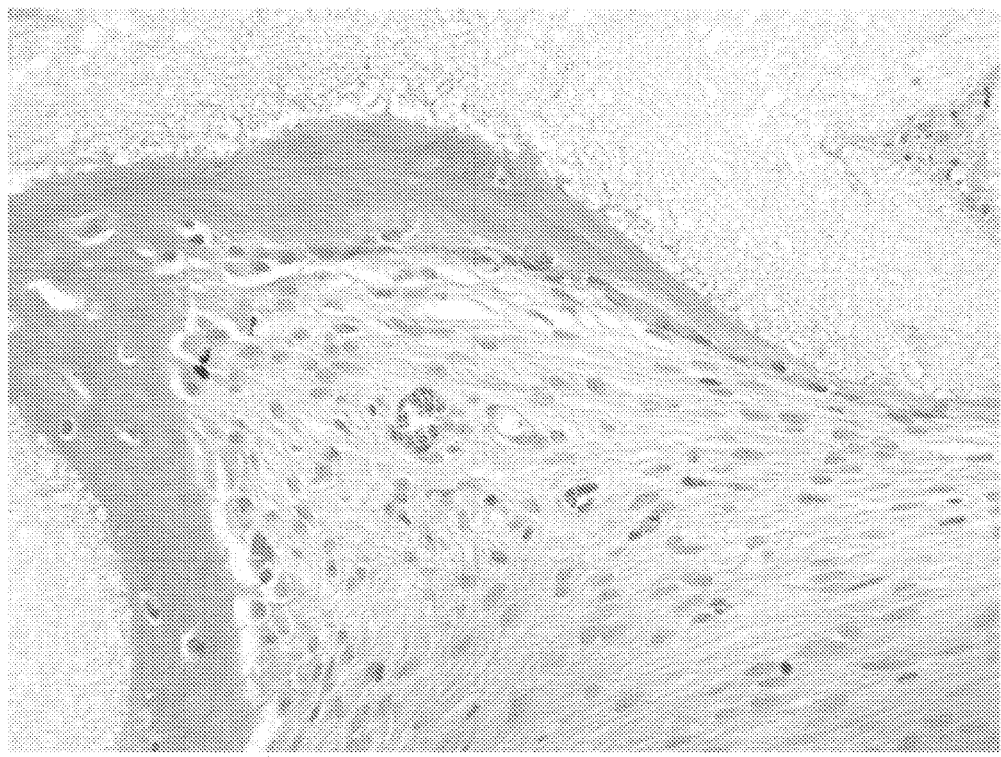
FIG. 24 is an image of H&E-stained section of human PDL cells stabilized in an AML vector.

The cells overexpressing amelogenin and vector control were seeded in the calcium phosphate scaffold (1 million cells per scaffold) and then implanted into the SCID mice for 6 weeks. The samples were harvested and sectioned. The tissue formation was demonstrated by H&E staining (see e.g., FIG. 23A-C'). The cementum like structure that connected to newly formed collagen fibers, similar to the structure of Sharpey's fibers was only observed in the PDL cells stabilized with an amelogenin vector (see e.g., FIG. 23A-A'''). FIG. 24 demonstrates another example from another donor forming the cementum-like structure.

Example 22

This example shows expression of amelogenin in PDL cells and cell differentiation.

Figures 25A, 25B, 25C, 25D, 25E:
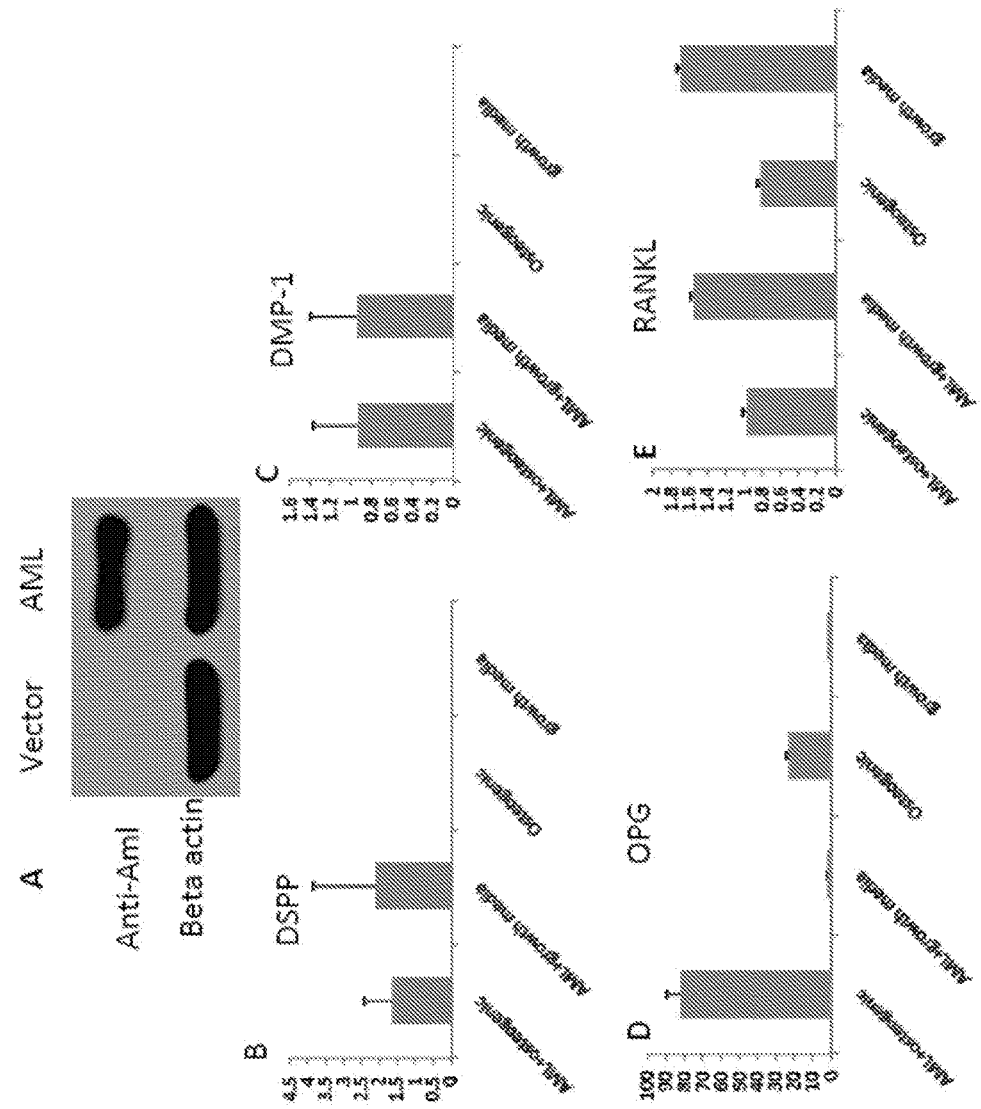
FIG. 25A is a western blot and FIG. 25B-25E is series of bar graphs describing cell differentiation in PDL cells.

Human dental pulp cells were transfected with amelogenin plasmid or vector. The cells were then subjected to G418 selection (300 mg/ml) for 2 weeks. The expression of amelogenin in PDL cells was confirmed by western blot (see e.g., FIG. 25A). The cell differentiation was measured by Real Time PCR (see e.g., FIG. 25 B-E).

Example 23

This example shows that cells overexpressing amelogenin (AML) were polarized in scaffolds.

Figures 26A, 26B, 26C:
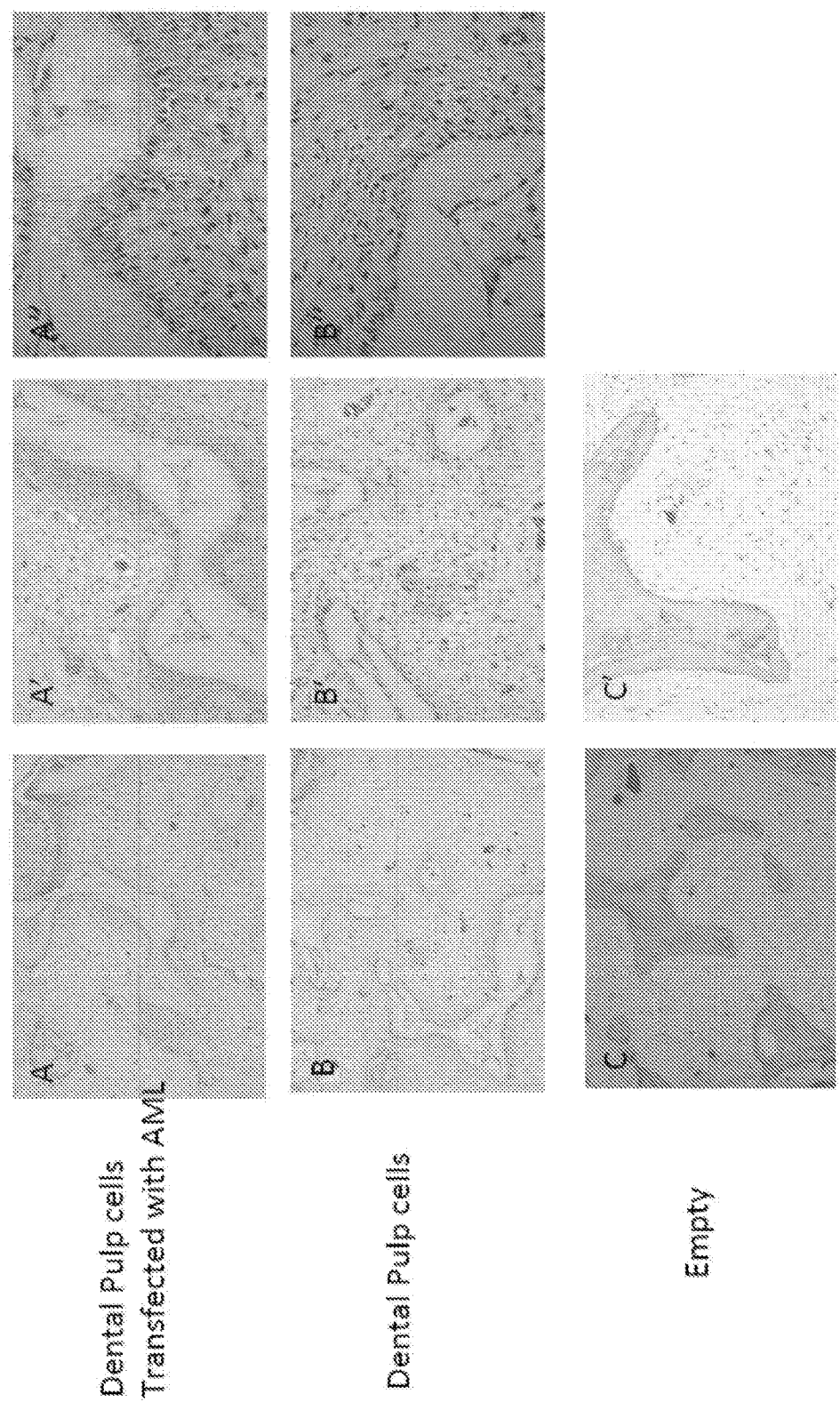
FIG. 26A-26C is a series of images of H&E-stained sections of dental pulp cells in scaffolds or empty scaffolds.

One million cells were seeded in the calcium phosphate scaffold and then implanted in SCID mice for 4 weeks. The scaffolds were sectioned and stained with H&E (see e.g., FIG. 26A-C'). The cells became polarized in scaffolds with the cells overexpressing amelogenin.

Example 24

This example shows amelogenin-treated dental pulp cells were DSP-positive.

Figures 27A, 27B:
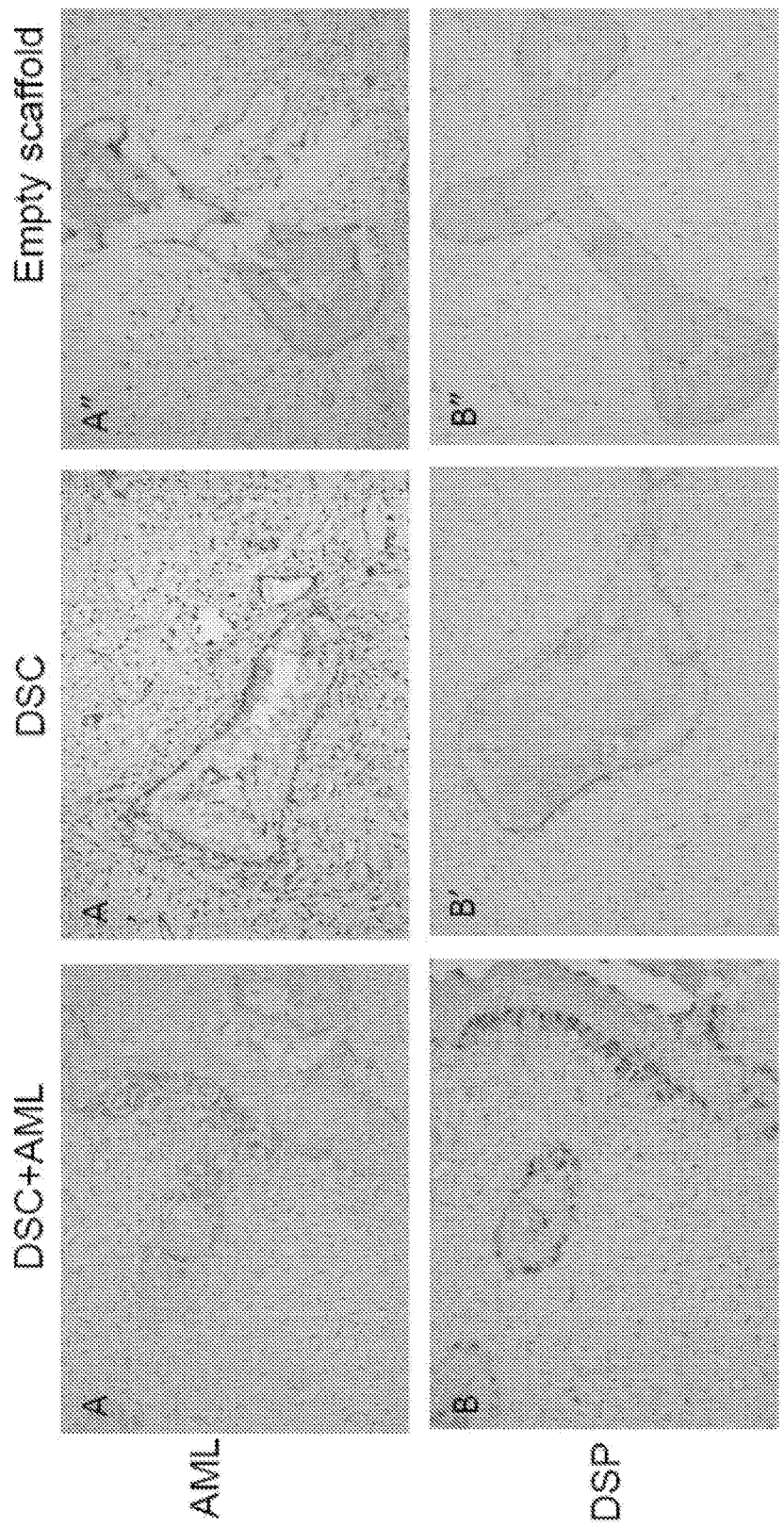
FIG. 27A-27B is a series of images of AML and DSP-stained cells treated with AML.

Immunostaining verified DSP-positive cells in the amelogenin group (see e.g., FIG. 27A-B").

Example 25

This example shows cell proliferation of amelogenin treated cells and amelogenin overexpression in cells.

Figure 28A:
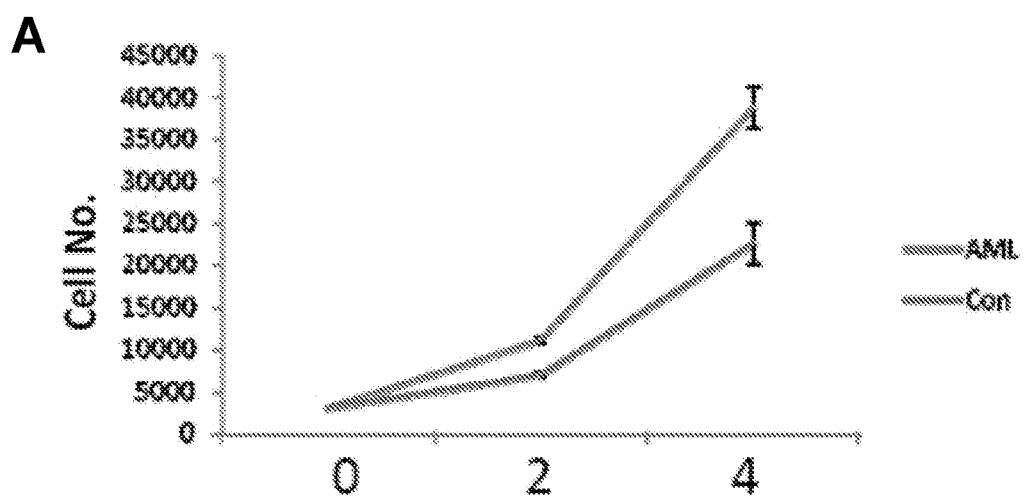
FIG. 28A-28B is a pair of graphs of cell count of DSCs at 0, 2, and 4 days post-treatment and stabilization of AML or control.
Figure 28B:
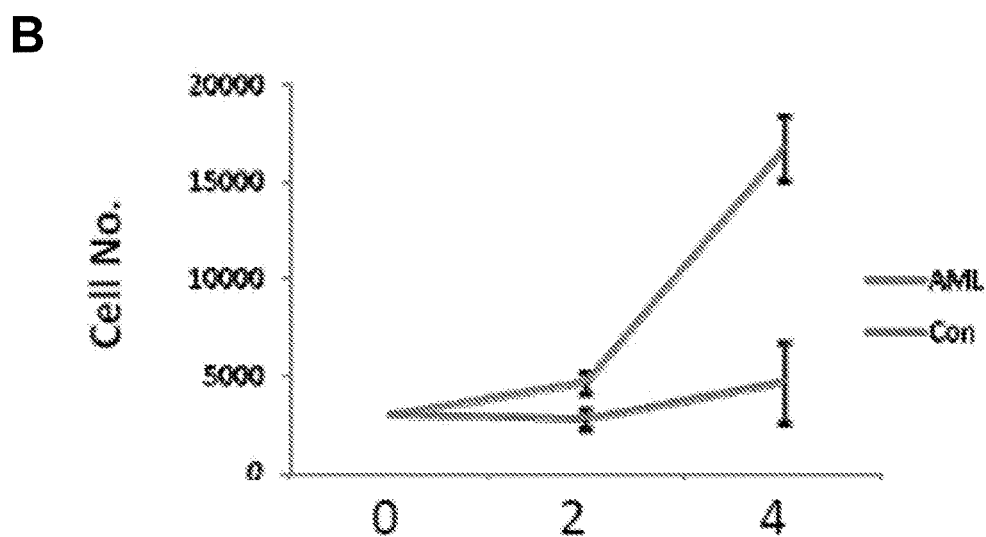
Figures 29A, 29B, 29C, 29D:
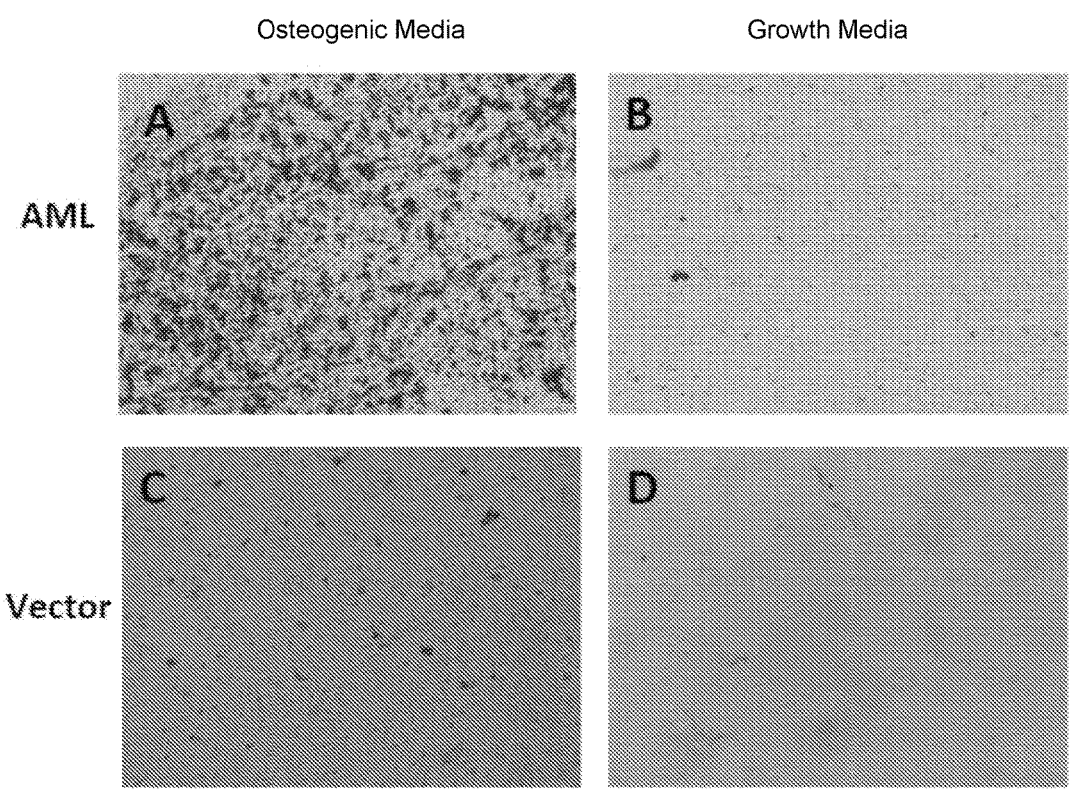
FIG. 29A-29D is a series of Van Kossa-stained images of DSCs after two weeks in media.

3000 cells were seeded in the 12 well plate and the cell number was counted every 2 days (see e.g., FIG. 28A-B). Both amelogenin treated cells and stabilized cells had more rapid proliferation.

Example 26

This example shows differentiation of DSC overexpressing amelogenin.

The cells were cultured in osteogenic media for 2 weeks and the cells differentiation was demonstrated by van Kossa staining (see e.g., FIG. 29A-D).

What is claimed is:

1. A method of forming a mineralized composition comprising:
    forming a mineralization composition comprising combining
        (i) ameloblasts;
        (ii) osteoblasts or odontoblasts; and
        (iii) an osteogenic medium comprising ascorbic acid and glycerophosphate; and
    adding amelogenin into the osteogenic medium in an amount sufficient to increase nuclear translocation of $\beta$-catenin, increase activation of $\beta$-catenin, or increase accumulation of non-phosphorylated $\beta$-catenin;
    culturing the mineralization composition under conditions suitable to induce production of a mineralized material; and
    forming a mineralized composition comprising enamel, dentin, or cementum.

2. The method of claim 1, wherein the amelogenin comprises naturally occurring or recombinant amelogenin.

3. The method of claim 1, wherein forming the mineralized composition further comprises:
    introducing the mineralization composition into a matrix material.

4. The method of claim 3, wherein the matrix material comprises a material selected from the group consisting of fibrin, fibrinogen, a collagen, a polyorthoester, a polyvinyl alcohol, a polyamide, a polycarbonate, a polyvinyl pyrrolidone, a marine adhesive protein, a cyanoacrylate, and a polymeric hydrogel, or a combination thereof.

5. The method of claim 3, wherein the matrix material comprises at least one physical channel.

6. The method of claim 3, wherein the (i) ameloblasts and (ii) osteoblasts or odontoblasts are independently present in the matrix material at a density of from about 0.0001 million cells per ml up to about 1000 million cells per ml.

7. The method of claim 3, wherein a ratio of the (i) ameloblasts to (ii) osteoblasts or odontoblasts in the matrix material is about 100:1 to about 1:100.

8. The method of claim 3, further comprising:
    introducing progenitor cells into the matrix material;
    differentiating at least a first portion of the progenitor cells to form the ameloblasts; and
    differentiating at least a second portion of the progenitor cells to form the osteoblasts or odontoblasts.

9. The method of claim 1, further comprising:
    differentiating a first plurality of progenitor cells to form the ameloblasts;
    differentiating a second plurality of progenitor cells to form the osteoblasts or odontoblasts; or
    differentiating progenitor cells to form the epithelial cells and mesenchymal cells.

10. The method of claim 9, wherein the progenitor cells comprise embryonic stem cells, umbilical cord stem cells, adult stem cells, dental stem cells, or induced pluripotent stem cells.

11. The method of claim 1, wherein culturing the mineralization composition comprises in vitro culturing.

12. The method of claim 1, wherein culturing the mineralization composition comprises in vitro culturing and mineralized material forms in a cell culture or matrix material.

13. The method of claim 1, wherein culturing the mineralization composition comprises in vivo culturing and mineralized material forms in a tissue or organ of a subject.

14. The method of claim 1, wherein said culturing the mineralization composition comprises in vivo culturing.

15. The method of claim 1, wherein:
    the ascorbic acid is present at a concentration of 50 µg/ml of the osteogenic medium; and
    the glycerophosphate is present at a concentration of 10 mM of the osteogenic medium.

16. The method of claim 1, wherein the osteogenic medium further comprises dexamethasone.

17. The method of claim 16, wherein the dexamethasone is present at a concentration of 1 mM of the osteogenic medium.

18. The method of claim 1, wherein the concentration of the amelogenin is 1 µg/ml, 3 µg/ml, or 5 µg/ml.

19. An engineered tissue composition comprising:
(a) ameloblasts;
(b) osteoblasts or odontoblasts;
(c) an osteogenic medium comprising ascorbic acid, glycerophosphate, dexamethasone, and
(d) adding amelogenin into the osteogenic medium in an amount sufficient to increase nuclear translocalization of β-catenin, increase activation of β-catenin, or increase accumulation of non-phosphorylated β-catenin; and
(e) a matrix material;
wherein,
the ameloblasts and the osteoblasts or odontoblasts are present in the matrix material;
the osteogenic medium is infused in the matrix material; and
the ameloblasts and the osteoblasts or odontoblasts are fluidly connected through the osteogenic medium.

20. The composition of claim 19, wherein at least one of the following is satisfied:
(i) the ameloblasts are differentiated from progenitor cells selected from the group consisting of embryonic stem cells, umbilical cord stem cells, adult stem cells, dental stem cells, and induced pluripotent stem cells;
(ii) the osteoblasts or odontoblasts are differentiated from progenitor cells selected from the group consisting of embryonic stem cells, umbilical cord stem cells, adult stem cells, dental stem cells, and induced pluripotent stem cells;
(iii) osteogenic medium comprises naturally occurring or recombinant amelogenin;
(iv) the matrix material comprises a material selected from the group consisting of fibrin, fibrinogen, a collagen, a polyorthoester, a polyvinyl alcohol, a polyamide, a polycarbonate, a polyvinyl pyrrolidone, a marine adhesive protein, a cyanoacrylate, and
a polymeric hydrogel, or a combination thereof;
(v) the matrix material comprises at least one physical channel;
(vi) the ameloblasts and the osteoblasts or odontoblasts are independently present in the matrix material at a density of from about 0.0001 million cells per ml up to about 1000 million cells per ml;
(vii) a ratio of the ameloblasts to the osteoblasts or odontoblasts in the matrix material is about 100:1 to about 1:100; or
(viii) the engineered tissue composition is suitable for in vitro culturing or in vivo culturing, or both.

21. The composition of claim 19, wherein:
the ascorbic acid is present at a concentration of 50 µg/ml of the osteogenic medium;
the glycerophosphate is present at a concentration of 10 mM of the osteogenic medium; and
the dexamethasone is present at a concentration of 1 mM of the osteogenic medium.

22. A method of treating a mineralization-related tissue or organ defect comprising grafting a composition according to claim 19 into a subject in need thereof.

23. A method of forming a mineralized composition comprising:
differentiating a first plurality of progenitor cells to form ameloblasts;
differentiating a second plurality of progenitor cells to form osteoblasts or odontoblasts;
forming a mineralization composition comprising combining
(i) the ameloblasts;
(ii) the osteoblasts or odontoblasts; and
(iii) an osteogenic medium comprising ascorbic acid and glycerophosphate;
adding amelogenin in an amount sufficient to increase nuclear translocalization of β-catenin, increase activation of β-catenin, or increase accumulation of non-phosphorylated β-catenin;
culturing the mineralization composition under conditions suitable to induce production of a mineralized material; and
forming a mineralized composition comprising enamel, dentin, or cementum.

24. A method of forming a mineralized composition comprising:
forming a first mineralization composition comprising ameloblasts in a first osteogenic medium comprising ascorbic acid and glycerophosphate;
forming a second mineralization composition comprising osteoblasts or odontoblasts in a second osteogenic medium comprising ascorbic acid and glycerophosphate; and
adding amelogenin into the first osteogenic medium and the second osteogenic medium in an amount sufficient to increase nuclear translocalization of β-catenin, increase activation of β-catenin, or increase accumulation of non-phosphorylated β-catenin;
culturing the first mineralization composition and the second mineralization composition under conditions suitable to induce production of a mineralized material;
introducing the first mineralization composition and the second mineralization composition into or onto a matrix material; and
forming a mineralized composition comprising enamel, dentin, or cementum.

* * * * *